(12) United States Patent
Toro Estrella et al.

(10) Patent No.: US 12,226,547 B2
(45) Date of Patent: Feb. 18, 2025

(54) 2D AND 3D BIOSCAFFOLD EXTRACELLULAR STRUCTURAL UNIT AND TISSUE STRUCTURE DESIGN AND METHODS OF MANUFACTURE

(71) Applicant: Ethicon, Inc., Somerville, NJ (US)

(72) Inventors: Hector Javier Toro Estrella, Somerville, NJ (US); Orquidea Helen Garcia, Somerville, NJ (US)

(73) Assignee: Ethicon, Inc, Somerville, NJ (US)

( * ) Notice: Subject to any disclaimer, the term of this patent is extended or adjusted under 35 U.S.C. 154(b) by 797 days.

(21) Appl. No.: 17/053,384

(22) PCT Filed: May 6, 2019

(86) PCT No.: PCT/US2019/030957
§ 371 (c)(1),
(2) Date: Nov. 6, 2020

(87) PCT Pub. No.: WO2019/217335
PCT Pub. Date: Nov. 14, 2019

(65) Prior Publication Data
US 2021/0369912 A1 Dec. 2, 2021

Related U.S. Application Data

(60) Provisional application No. 62/668,203, filed on May 7, 2018.

(51) Int. Cl.
| A61L 27/24 | (2006.01) |
| A61L 27/18 | (2006.01) |
| A61L 27/26 | (2006.01) |
| A61L 27/34 | (2006.01) |
| A61L 27/36 | (2006.01) |
| A61L 27/56 | (2006.01) |
| B33Y 10/00 | (2015.01) |
| B33Y 80/00 | (2015.01) |

(52) U.S. Cl.
CPC ............... *A61L 27/24* (2013.01); *A61L 27/18* (2013.01); *A61L 27/26* (2013.01); *A61L 27/34* (2013.01); *A61L 27/3633* (2013.01); *A61L 27/56* (2013.01); *B33Y 10/00* (2014.12); *B33Y 80/00* (2014.12); *A61L 2430/04* (2013.01)

(58) Field of Classification Search
CPC ...... A61L 27/24; A61L 27/3633; A61L 27/56; C12M 25/14
See application file for complete search history.

(56) References Cited

U.S. PATENT DOCUMENTS

| 6,702,848 | B1 * | 3/2004 | Zilla ........................ A61F 2/06 623/1.39 |
| 6,730,252 | B1 | 5/2004 | Teoh et al. |
| 7,371,400 | B2 | 5/2008 | Borenstein et al. |
| 9,757,132 | B2 * | 9/2017 | Laurencin ................. A61F 2/08 |
| 2001/0051824 | A1 | 12/2001 | Hopkins et al. |
| 2003/0055502 | A1 | 3/2003 | Lang et al. |
| 2003/0069718 | A1 | 4/2003 | Hollister et al. |
| 2004/0059356 | A1 * | 3/2004 | Gingras ................ A61F 2/0077 606/151 |
| 2004/0236424 | A1 | 11/2004 | Berez et al. |
| 2005/0043813 | A1 | 2/2005 | Kusanagi et al. |
| 2007/0014729 | A1 | 1/2007 | Farhat et al. |
| 2008/0004713 | A1 | 1/2008 | Nakamura et al. |
| 2008/0091234 | A1 * | 4/2008 | Kladakis ................. B29C 59/14 264/129 |
| 2008/0097601 | A1 | 4/2008 | Codori-Hurff et al. |
| 2009/0148486 | A1 | 6/2009 | Lu et al. |
| 2010/0212138 | A1 | 8/2010 | Carroll et al. |
| 2010/0292791 | A1 * | 11/2010 | Lu ........................... A61P 37/06 623/13.12 |
| 2012/0189586 | A1 | 7/2012 | Harrell |
| 2012/0271418 | A1 | 10/2012 | Hollister et al. |
| 2013/0238096 | A1 | 9/2013 | Kotlus |
| 2015/0080320 | A1 | 3/2015 | Desai |
| 2016/0022416 | A1 | 1/2016 | Felix et al. |
| 2016/0186131 | A1 | 6/2016 | Voytik-Harbin |
| 2016/0199538 | A1 * | 7/2016 | Schussler ................ A61L 27/24 435/402 |
| 2016/0243762 | A1 | 8/2016 | Fleming et al. |
| 2016/0256259 | A1 | 9/2016 | Wirth et al. |
| 2017/0071747 | A1 | 3/2017 | Shidid et al. |
| 2017/0281367 | A1 | 10/2017 | Ketchum et al. |
| 2017/0304492 | A1 * | 10/2017 | Iwai ........................ A61L 27/54 |
| 2017/0360578 | A1 | 12/2017 | Shin et al. |

(Continued)

FOREIGN PATENT DOCUMENTS

| CN | 107802888 A | 3/2018 |
| EP | 1982735 A1 | 10/2008 |

(Continued)

OTHER PUBLICATIONS

International Search Report for International Application No. PCT/US2019/030960, dated Aug. 30, 2019, 3 pages.
International Search Report , PCT/US2019/030959—dated Aug. 26, 2019, 3 pages.
PCT/US2019/030957—International Search Report dated Aug. 26, 2019.
Yong He et al.,, A 3D-Printed PLCL Scaffold Coated with Collagen Type I and Its Biocompatibility, Biomed Research International, vol. 2018, Jan. 1, 2018, pp. 1-10.
Dafydd O. Visscher et al., "Cartilage Tissue Engineering: Preventing Tissue Scaffold Contraction Using a 3D-Printed Polymeric Cage," Tissue Engineering, Part C, Methods, Dec. 2008, vol. 22, No. 6, Jun. 1, 2016, pp. 573-584.

(Continued)

*Primary Examiner* — Andrew S Rosenthal
(74) *Attorney, Agent, or Firm* — Goodwin Procter LLP

(57) ABSTRACT

A bioscaffold structure is provided, the bioscaffold comprising a plurality of connected unit cells, each unit cell comprising a plurality of filaments composed of an extracellular material containing Collagen I and Collagen III, wherein each of the plurality of unit cells includes at least one opening connected to an internal volume.

30 Claims, 14 Drawing Sheets

(56) References Cited

U.S. PATENT DOCUMENTS

| | | |
|---|---|---|
| 2019/0133653 A1 | 5/2019 | Swarts |
| 2019/0151081 A1 | 5/2019 | Limem et al. |
| 2019/0247174 A1* | 8/2019 | Zegarelli ............. A61C 19/063 |
| 2021/0228772 A1 | 7/2021 | Toro Estrella et al. |
| 2021/0369912 A1 | 12/2021 | Toro Estrella et al. |

FOREIGN PATENT DOCUMENTS

| | | |
|---|---|---|
| EP | 3813897 A1 | 5/2021 |
| RU | 2598769 C1 | 9/2016 |
| WO | 2007/136634 A1 | 11/2007 |
| WO | 2019/217335 A1 | 11/2019 |
| WO | 2019/217337 A1 | 11/2019 |
| WO | 2019/217338 A1 | 11/2019 |

OTHER PUBLICATIONS

Minqiang et al., Chinese Oncology Clinical Yearbook, Zhao Ping edit, Beijing: Peking Union Medical College Press, 1st Edition, Sep. 30, 2006, 10 pages.

Hackett, et al. "Electrospun Biocomposite Polycaprolactone/Collagen Tubes as Scaffolds for Neural Stem Cell Differentiation," Materials, 2010, 3:3714-3728.

* cited by examiner

2D AND 3D BIOSCAFFOLD EXTRACELLULAR STRUCTURAL UNIT AND TISSUE STRUCTURE DESIGN AND METHODS OF MANUFACTURE

CROSS-REFERENCE TO RELATED APPLICATION

This application is an international application claiming the benefit of priority from U.S. Provisional Application No. 62/668,203 filed on May 7, 2018, the entirety of which is incorporated herein by reference.

FIELD

The embodiments disclosed herein are generally directed towards porous extracellular structures and/or bioscaffold structures that can include unit cells and methods for manufacturing said structures. More specifically, there is a need for porous extracellular structures and/or bioscaffold structures that have a porous construct suited to promote optimal cellular infiltration, tissue regeneration and minimize risk of adverse immune response in and/or pathogenic contamination to the patient.

BACKGROUND

The embodiments disclosed herein are generally directed towards three-dimensional porous extracellular structures and/or bioscaffold structures for optimal cellular infiltration and methods for producing said structures. Bioscaffold structures are usually extracellular constructs that can be used to replace the structure and/or function of an organ or tissue on a temporary or permanent basis. The goal of bioscaffold structures can be to aid the restoration of normal function or appearance of the involved organ or tissue. The bioscaffold structure can accomplish this goal by providing a platform from where cells can infiltrate and overtake. This can result in the cells replacing the bioscaffold structure while restoring and/or improving organ or tissue function and/or appearance.

To provide a bioscaffold structure suited for optimal cellular infiltration, the bioscaffold generally can include a series of pores that allow for cellular ingrowth. The bioscaffold can also be composed of materials that allow for the requisite biodegradation and bioresorbtion as the cellular ingrowth replaces the bioscaffold and restores organ or tissue function and/or appearance. Those materials, however, should not induce adverse biological responses. The bioscaffold will also have an optimal tensile strength to withstand the stresses of initial implantation, in vivo physiologic requirements and subsequent infiltration. The bioscaffold composition can also possess surface chemistry properties to allow for requisite cell adherence.

Conventional bioscaffolds are manufactured from extracellular matrices (ECM) that are manufactured out of tissue extracted from human cadavers or porcine (pig) products and later decellularized to leave the intact extracellular matrix. When sourced from the dermis (skin) these scaffolds are known as acellular dermal matrices (ADM).

However, these conventional extracellular matrix materials can have a number of potential drawbacks. The materials can trigger immunogenic responses when they are implanted into a patient as the materials may have residual cellular or extracellular components from the donor source. Moreover, since the ADM materials are typically taken from adult or elderly donors, the materials can contain excessively high ratios of Collagen I to Collagen III which provides decreased structural support, cushioning, protection, reinforcement and coverage than tissues containing lower Collagen I to Collagen III ratios.

Besides producing adverse biological responses, conventional bioscaffolds often fail to provide optimal compositions of extracellular matrix proteins (e.g., collagen, elastin, laminin, cytokines, polysaccharides, growth factors, etc.) that help promote cell ingrowth into the bioscaffolds and thus boosting overall tissue regeneration which can help in patient recovery and reducing overall scarring.

Besides failing to provide an optimal mixture of extracellular matrix proteins to promote cell ingrowth and tissue regeneration, conventional ADM bioscaffolds can fail to properly balance the requisite pore size and structure to promote optimal cell and tissue growth and vascularization against providing sufficient structural properties (such as tensile strength and elasticity) required to withstand regular bioscaffold use scenarios such as, for example, suturing and expansion. Moreover, it is apparent that the cellular niche (size, shape, substrate, etc.), rather than the cell itself, that can ultimately direct and control a cell's fate. As such, the architecture of the cellular niche provided for host cell infiltration will ultimately influence the molecular and mechanical signals that will direct cellular behavior.

Moreover, since conventional ADM bioscaffolds are typically come as non-customizable two-sheets of material, they can require extensive handling or manipulation (e.g., cutting, shaping, stitching, etc.) by the surgeon prior to implantation into a patient. This may lead to an increase in risk of contamination to the patient.

Accordingly, there is a need to develop two-dimensional and three-dimensional porous extracellular structures and/or bioscaffold structures that minimize host immunogenic response and better promote cell growth while maintaining sufficient mechanical properties. Moreover, there is a need to provide means to precisely control the architecture and size of the produced cell niche, to therefore enable the optimal geometric unit within the extracellular construct to promote cellular infiltration, remodeling and tip cell fate with regenerative response rather than fibrotic response.

SUMMARY

In one aspect, a bioscaffold structure is provided, the bioscaffold comprising a plurality of connected unit cells, each unit cell comprising a plurality of filaments composed of an extracellular material containing Collagen I and Collagen III, wherein each of the plurality of unit cells includes at least one opening connected to an internal volume.

In another aspect, a bioscaffold structure is provided, the bioscaffold comprising a layer of filaments composed of an extracellular material containing Collagen I and Collagen III, wherein the layer includes a plurality of pores.

In a further aspect, a method for producing a bioscaffold structure is provided, the method comprising depositing droplets of a liquefied polymer onto a substrate surface to form a bioscaffold structure comprising a plurality of connected unit cells (wherein each of the plurality of unit cells includes at least one opening connected to an internal volume) and applying a coating of Collagen I and Collagen III onto the bioscaffold structure.

In another aspect, a method for producing a bioscaffold structure is provided, the method comprising applying a stream liquefied polymer onto a substrate surface to form a bioscaffold structure comprising a plurality of connected unit cells (wherein each of the plurality of unit cells includes at least one opening connected to an internal volume) and applying a coating of Collagen I and Collagen III onto the bioscaffold structure.

In yet another aspect, a method for producing a bioscaffold structure is provided, the method comprising supplying a stream of liquefied polymer though a heated nozzle, generating an electric field to draw the stream of liquefied polymer to a collector plate, depositing a plurality of streams of liquefied polymer onto the collector plate to form a bioscaffold structure comprising a plurality of connected unit cells (wherein each of the plurality of unit cells includes at least one opening connected to an internal volume) and applying a coating of Collagen I and Collagen III onto the bioscaffold structure.

Additional aspects will be evident from the detailed description which follows, as well as the claims appended hereto and the drawings.

BRIEF DESCRIPTION OF THE DRAWINGS

For a more complete understanding of the principles disclosed herein, and the advantages thereof, reference is now made to the following descriptions taken in conjunction with the accompanying drawings, in which.

Figure 1A:
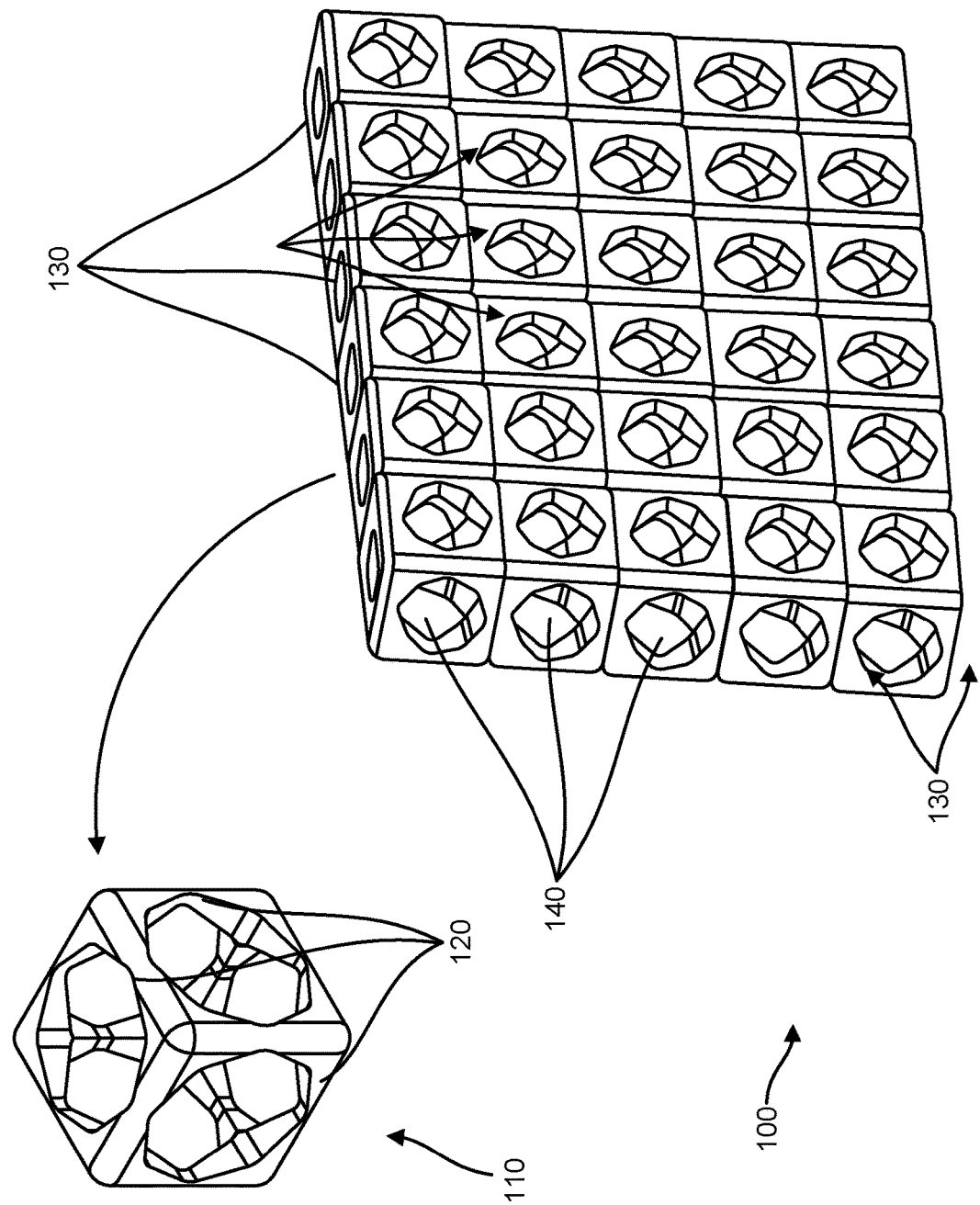
FIGS. 1a to 1e illustrates various bioscaffold structures comprised of different types of unit cell structures, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

This specification describes exemplary embodiments and applications of the disclosure. The disclosure, however, is not limited to these exemplary embodiments and applications or to the manner in which the exemplary embodiments and applications operate or are described herein. Other embodiments, features, objects, and advantages of the present teachings will be apparent from the description and accompanying drawings, and from the claims. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, a tray, a baseplate, a separate metal structure, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "extracellular", as used in reference to, for example, "extracellular material", "extracellular structure", "extracellular matrix", "extracellular construct", and "extracellular component", denotes the characteristic of existing outside the cell and can refer to a synthetic or natural material. Examples of materials that are extracellular include synthetic and natural polymers; metabolites; ions; various proteins and non-protein substances (e.g. DNA, RNA, lipids, microbial products, etc.) such as collagens, proteoglycans, hormones, growth factors, cytokines, chemokines; various enzymes including, for example, digestive enzymes (e.g., Trypsin and Pepsin), extracellular proteinases (e.g., matrix metalloproteinases, a disintegrin and metalloproteinase with thrombospondin motifs (ADAMTSs), Cathepsins) and antioxidant enzymes (e.g., extracellular superoxide dismutase); proteolytic products; extracellular matrix proteins (such as elastin, glycosaminoglycans (GAGs), laminin, fibronectin, etc.), selected cell populations, small molecules and small molecule inhibitors, antibiotics, antimicrobials, nanoparticles, mesoporous silica, silk fibroin, enzymatic degradation sites; anti-fibrotic agents such as anti-transforming growth factor beta (anti-TGF-β) and anti-tumor necrosis factor alpha (anti-TNF-α); pro-angiogenic agents such as vascular endothelial growth factor (VEGF) and placental growth factor (PlGF); and factors affecting adipogenesis and proliferation such as insulin-like growth factor 1 (IGF-1) and Dexamethasone.

As used herein, "bioink" denotes any bioactive, bioprintable, naturally or artificially derived material that mimics an extracellular matrix environment to support the adhesion, proliferation, and differentiation of living cells, and can be deposited as filaments, fibers or fibrils during an additive manufacturing process.

As used herein, "bioscaffold" denotes a biocompatible and bioresorbable structure used in tissue engineering that is capable of being implanted in the body in order to promote cell adhesion and tissue regeneration, often for injury recovery. A bioscaffold can be used, for example, in the areas of bone, cartilage, skin, organ, tissue area/volume (e.g., breast tissue), and muscle regeneration.

As used herein, "angular range" denotes a range of angles by which two objects can be placed relative to each other.

As used herein, the terms "comprise", "comprises", "comprising", "contain", "contains", "containing", "have", "having" "include", "includes", and "including" and their variants are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus.

Unless otherwise defined, scientific and technical terms used in connection with the present teachings described herein shall have the meanings that are commonly understood by those of ordinary skill in the art.

The present disclosure relates to porous two-dimensional and three-dimensional extracellular structures and/or bioscaffolds and methods for manufacturing them. These porous extracellular structures have a variety of useful applications, particularly medical applications. With respect to medical applications, porous extracellular structures, such as bioscaffolds, are uniquely suited for promoting cellular infiltration in medical implants including, for example, breast implants related to breast oncology. Such structures provide a platform for tissue reinforcement. The porous nature of these structures can allow an implant to promote cellular growth within the region of interest while providing the required structural integrity to withstand the stresses accompanying implantation procedures (e.g., suturing, cutting, shaping, etc.) and subsequent expansion and cellular infiltration.

Figure 1B:
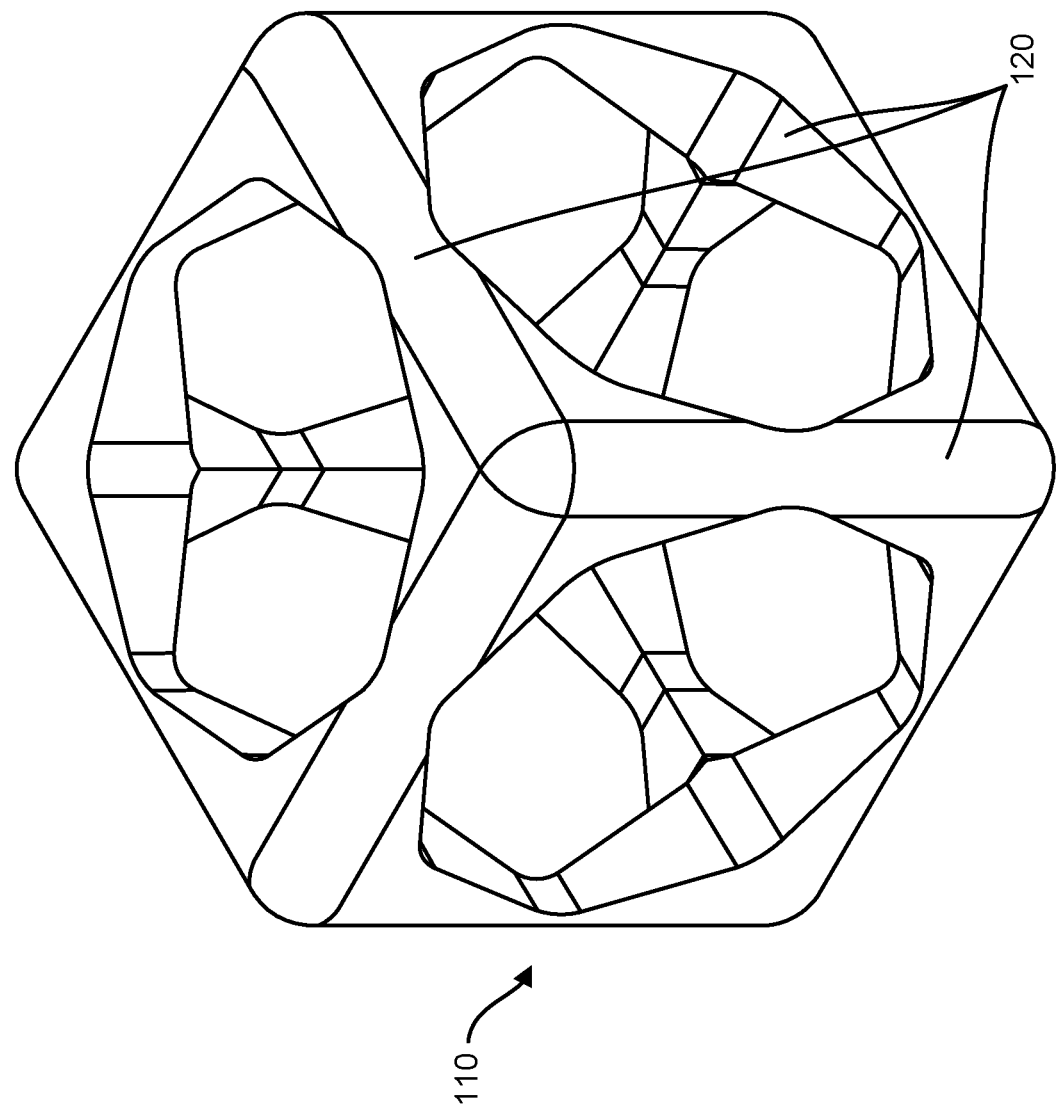
Figure 1C:
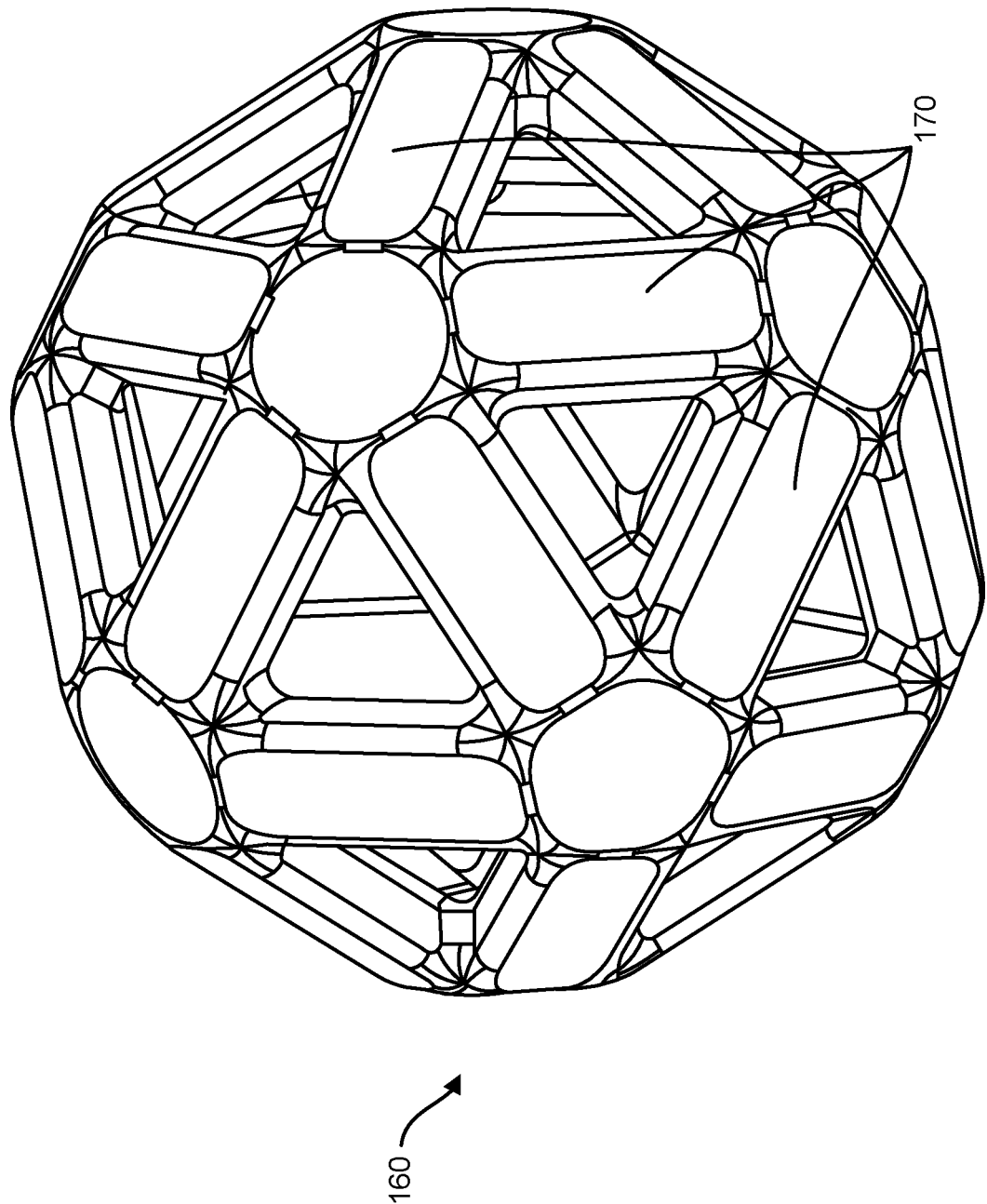
Figure 1D:
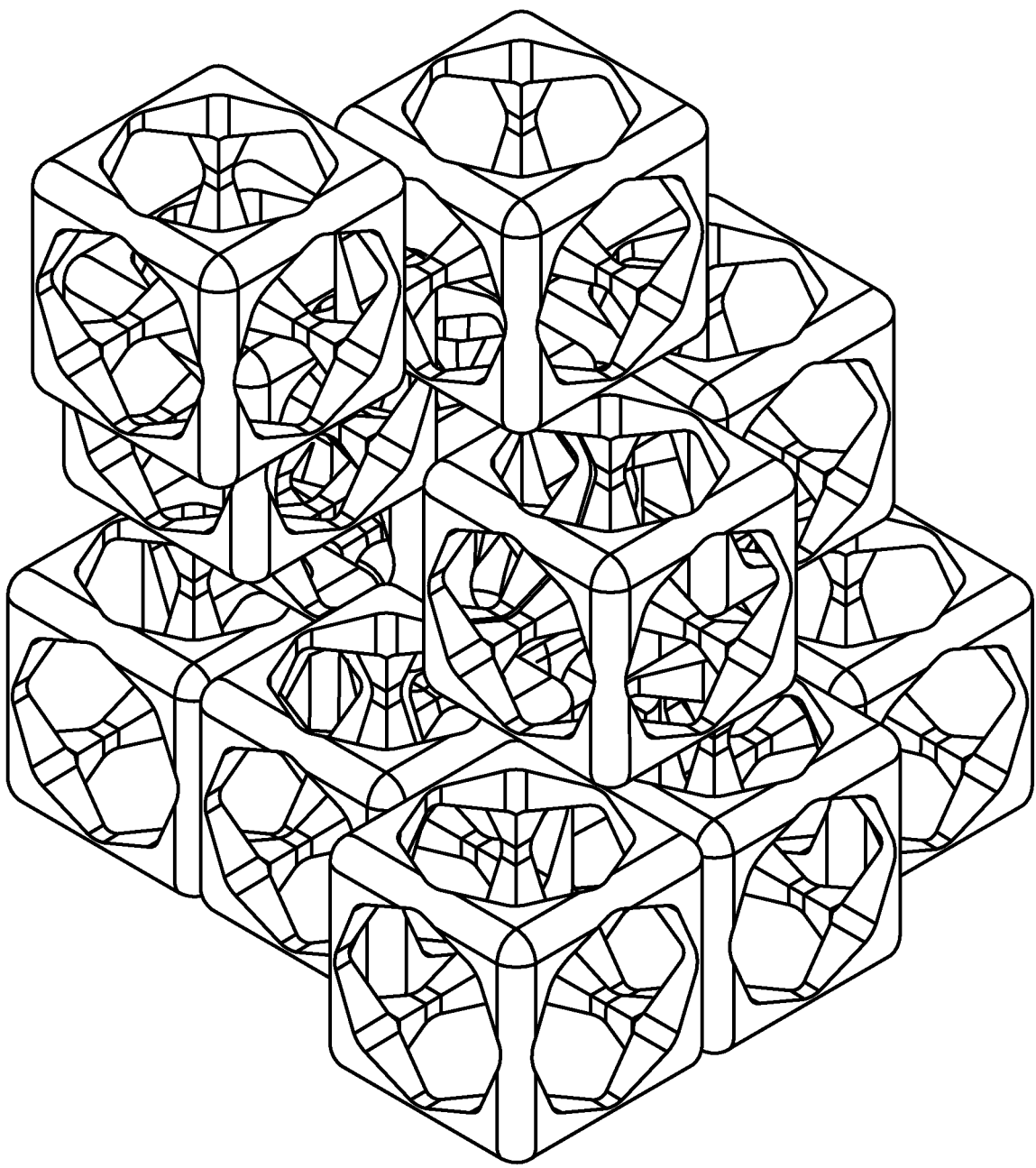
Figure 1E:
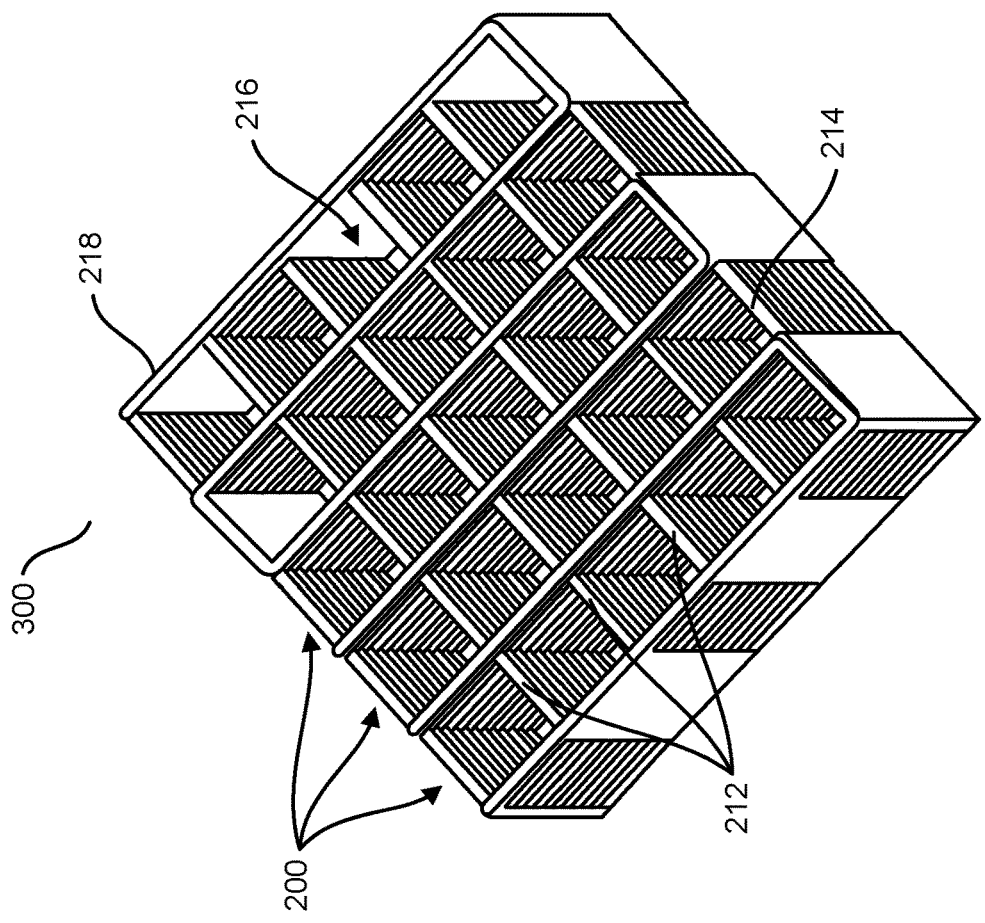
Figure 1E:
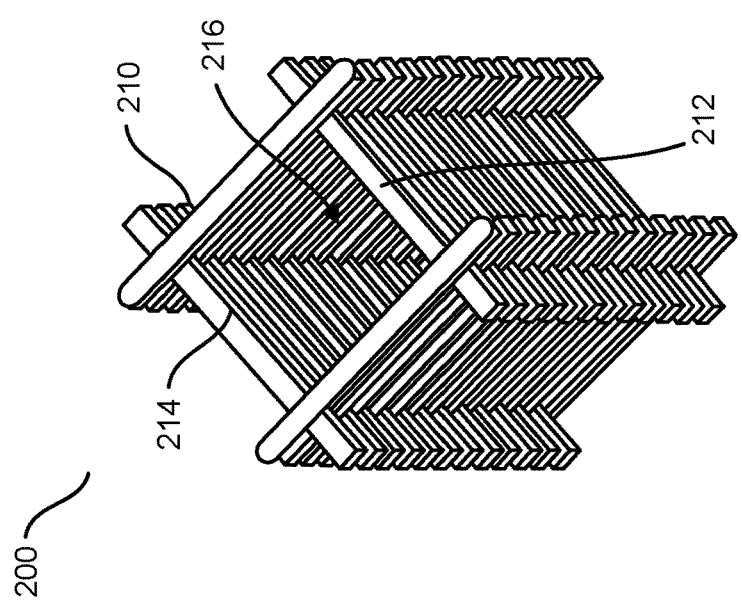

In accordance with various embodiments, a bioscaffold structure is provided as illustrated, for example, by structure 100 of FIG. 1a. Structure 100 can comprise a plurality of connected unit cells 110. Each unit cell 110 can comprise a plurality of filaments 120 composed of an extracellular material containing natural (e.g., polysaccharides, lipids, proteins, etc.) or artificial polymers (e.g., polycaprolactone, polyethylene glycol, ethylene propylene, polyethylene terephthalate, etc.), collagens, (e.g., Collagen I, Collagen II, Collagen III, Collagen IV, Collagen V, etc.). Further, each of the plurality of unit cells 110 can include at least one opening 130 connected to an internal volume 140. For an enlarged view of a unit cell 110, see FIG. 1b, which shows the unit cell structure only. For another example of a unit cell structure with a different unit cell geometry from unit cell 110 of FIGS. 1a and 1b, see unit cell 160 of FIG. 1c depicting a hexagonal polyhedron, which can be comprise of a plurality of filaments (or struts) 170. For yet another example of a unit cell structure, see FIG. 1e, which shows a unit cell 200 which is comprised of a four-sided structure with opposite sided openings 214 connected to an internal volume 216. In various embodiments, each side of the four-sided structure is formed from a stack of filaments 212 (struts). Further, as depicted in FIG. 1e, a bioscaffold structure 300 can be comprised of a plurality of these unit cells 200.

The putative geometries that cells will encounter may be homogenous or heterogeneous interconnected structures with fibrils 210 and openings 214 (pores) that may be spaced in the nm or μm range. Specific geometries can be achieved through the printing of fibrils 210 in a raster pattern 218, for example, a continuous or semi-continuous printing of fibrils 210 with raster angles of between about 10 degree to about 90 degree orientations of each other to form a network of cellular geometries that can include, for example but are not limited to, triangles, quadrilaterals, concave and convex polygons, regular and irregular polygons, curved 2D and 3D shapes, and platonic solids.

In various embodiments, the extracellular material of the bioscaffold structure can contain a Collagen I to Collagen III ratio similar to those contained within human dermis (e.g., fetal, adolescent, adult and elderly) as shown in Table I.

TABLE I

| Dermis Type | Collagen I/III Ratio |
| --- | --- |
| Fetus | 0.95 ± 0.03 |
| Adolescent | 2.27 ± 0.13 |
| Adult | 2.46 ± 0.15 |
| Elderly | 2.97 ± 0.40 |

That is, in various embodiments, the extracellular material can have a Collagen I to Collagen III ratio in the range of between about 0.5 to about 3.5, or in the range of between about 0.75 to about 3.0, or in the preferred range of between about 0.9 to about 2.5. The preferred Collagen I to Collagen III ratio range of between about 0.9 to about 2.5 may offer advantages against conventional tissue offerings, which are predominantly taken from adult and elderly donors, contain much higher ratios of Collagen I to Collagen III, thereby providing decreased support, cushioning, protection, reinforcement and covering than do tissues containing lower ratios.

More specific ratios of Collagen I to Collagen III can be about 0.5, about 0.55, about 0.6, about 0.65, about 0.7, about 0.75, about 0.8, about 0.85, about 0.9, about 0.95, about 1.0, about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 1.95, about 2.0, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3.0, about 3.05, about 3.1, about 3.15, about 3.2, about 3.25, about 3.3, about 2.35, about 3.4, about 3.45, about 3.5 and ranges between any two of these values.

Collagen I and Collagen III can help provide a platform for infiltrating cells to attach to the bioscaffold structure, by providing an extensive network of extracellular matrix cues that provide an appropriate cell niche for host cell receptor recognition, in-growth, vascularization and remodeling within the breast, other organs, or other anatomy and surrounding tissues currently unattainable in synthetic matrix offerings. Collagen I and Collagen III can also aide in directing cell fate and differentiation. Identification of these collagen components by cell surface receptors induce the production of signaling molecules needed for tissue generation and scaffold remodeling.

The extracellular material can further be comprise of bioactive materials. These bioactive materials can include, but are not limited to, other types of collagen (e.g., Collagen II, IV, V, VI, etc.), extracellular matrix proteins (such as elastin, glycosaminoglycans (GAGs), laminin, fibronectin, etc.), growth factors, cytokines, polysaccharides, selected cell populations, small molecules and small molecule inhibitors, antibiotics, antimicrobials, nanoparticles, mesoporous silica, silk fibroin, enzymatic degradation sites, and any combination thereof. Anti-fibrotic agents can be included in the extracellular material, with examples such as anti-transforming growth factor beta (anti-TGF-β) and anti-tumor necrosis factor alpha (anti-TNF-α). Pro-angiogenic agents can be included in the extracellular material, with examples such as vascular endothelial growth factor (VEGF) and placental growth factor (PlGF). Factors affecting adipogenesis and proliferation can be included in the extracellular material, with examples such as insulin-like growth factor 1 (IGF-1) and dexamethasone.

The at least one opening (130 or 214) can have a diameter of between about 100 microns (μm) to about 500 microns. Alternatively, the at least one opening can be a shape other than circular, wherein the at least one opening can have a length of between about 50 microns to about 1000 microns, or about 50 microns to about 500 microns, or about 100 microns to 1000 microns. Each filament of the bioscaffold structure can have a diameter of less than or equal to about 100 microns.

In order to allow for appropriate tissue ingrowth, the size of the at least one opening, as well as the orientation of multiple openings in relation to each other and their geometry, can be important. Openings (i.e., pores) should be large enough to accommodate the size and geometry of the infiltrating cell, but small enough so that infiltrating cells can attach to the bioscaffold structure, and to each other, to form complex interconnected cellular signaling networks, allowing for scaffold degradation, collagen synthesis and tissue regeneration. As such, the material must be "spongy" enough to allow cellular infiltration throughout the entire construct (length, width, height and depth). For example, as applied to human skin, human dermal fibroblasts are typically approximately 30-70 microns in width. Therefore, it was determined that a pore size from about 100 microns to about 500 microns will allow cellular infiltration, while still providing a niche in which cells are able to communicate via membrane or cytokine signaling. In various embodiments, the pore size can be about 50 microns to about 1000 microns, or about 50 microns to about 500 microns, or about 100 microns to about 1000 microns.

The extracellular material of the bioscaffold structure can also contain one or more polymers. The polymer can be a dissolvable polymer. The polymer can be natural or synthetic. Examples of polymers include polyethylene glycol (PEG), Poly(lactide-co-clycolide) (PLGA), polycaprolactone (PCL), poly(l-lactic acid (PLLA), ethylene propylene, polyethylene terephthalate, alginate, polysaccharide, hyaluronic acid, gelatin, soy protein, fibrinogen, chitosan, dextran, starch or another type of polymer. In various embodiments, the polymer can be just PCL.

While it is generally unattainable with conventional tissue matrix offerings, the use of natural and/or synthetic polymers as discussed above can assist in providing mechanical stability to the bioscaffold and result in a consistent bioscaffold degradation profile that allows plastic and reconstructive surgeons the ability to better predict and control clinical outcomes in patients.

Figure 2:
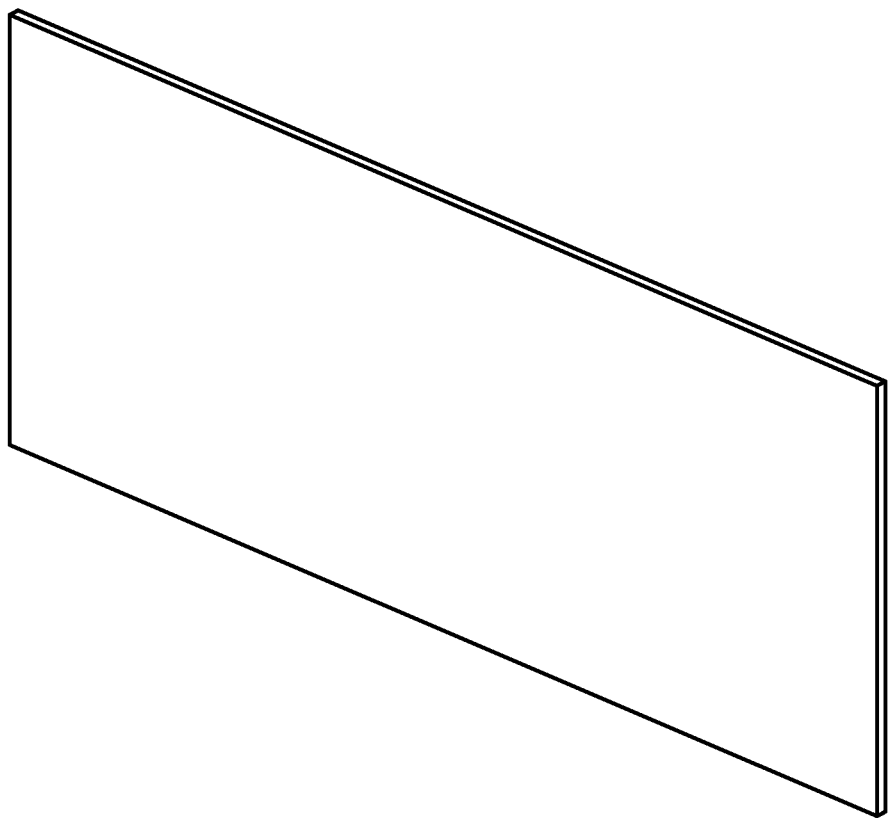
FIG. 2 illustrates a flat sheet bioscaffold implant, in accordance with various embodiments.
Figure 3:
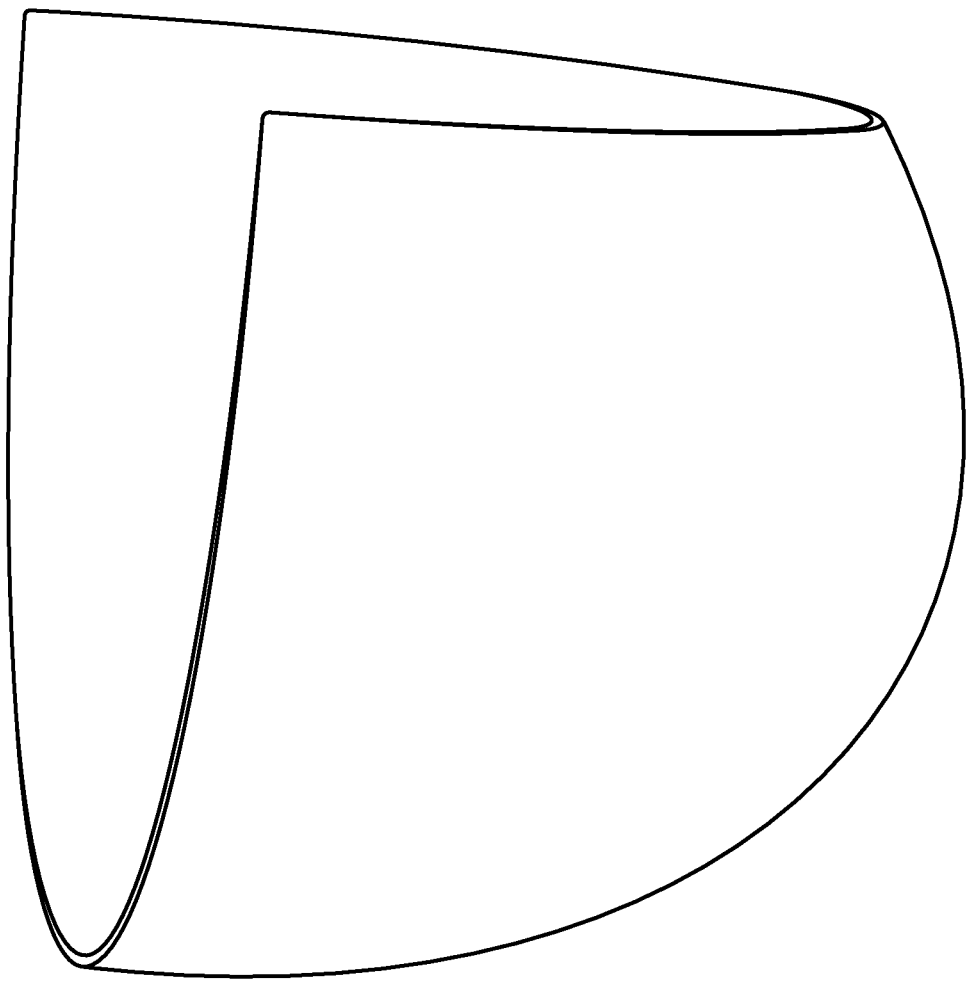
FIG. 3 illustrates a hand in glove fit bioscaffold implant, in accordance with various embodiments.
Figure 4:
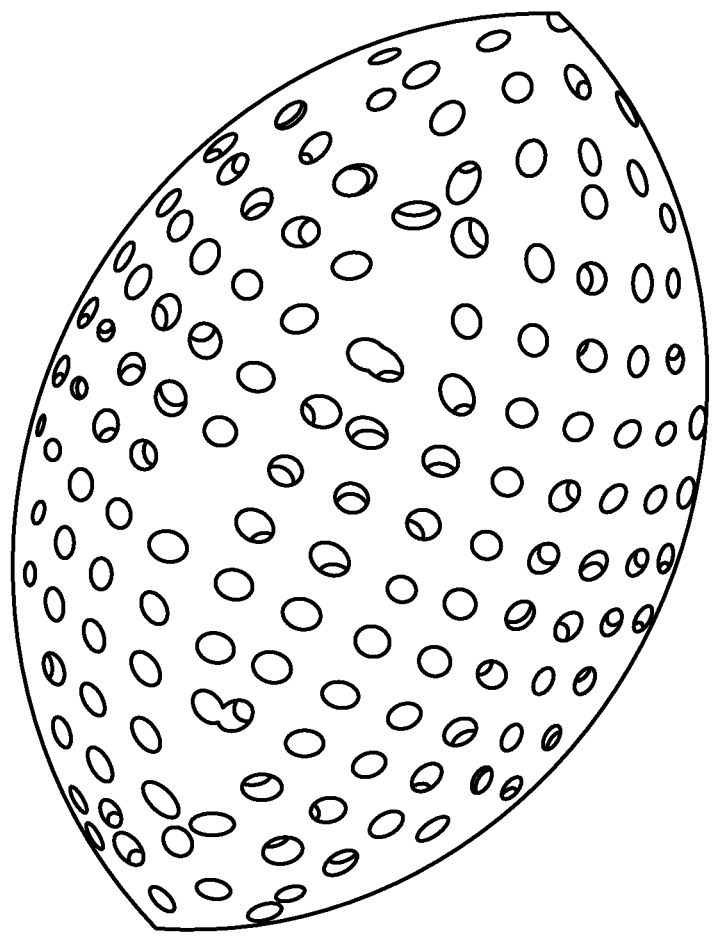
FIG. 4 illustrates a ready-to-use bioscaffold implant, in accordance with various embodiments.

The plurality of connected unit cells in the bioscaffold structure can form a substantially planar sheet as depicted in FIG. 2. The plurality of connected unit cells in the bioscaffold structure can also form a 3D macrostructure as depicted in FIGS. 3 and 4. Further, the bioscaffold structure can have a thickness of between about 0.5 mm to about 200 mm, or between about 0.5 mm to about 20 mm, or between about 0.5 mm to about 2.5 mm. The 3D macrostructure can include, for example, a "hand in glove" fit configuration (FIG. 3) and a "ready-to-use" solid implant configuration (FIG. 4) discussed in more detail below.

Regarding unit cell geometry and scaffold design, the specific geometries of the unit cells can correlate to the size and arrangement of the bioprinted filaments (struts) that make up the unit cell, as well as the arrangement of the openings (pores) and the opening size (pore size) created by material deposition (the material deposition processes are discussed in more detail below). Cellular fate and function can be dictated by the fiber (fibril) size (e.g., diameter of deposited thread or strand of polymer and/or bioink material, discussed in more detail below), pore size of the overall matrix (e.g., individual planar and non-planar sheet, or plurality of sheets, that make up the implant), matrix density/height, base polymer (if used), extracellular material composition, and the use/interplay between a standardized pore structure (e.g., of the overall matrix) and/or the random arrangement of pore structures (e.g., of the overall matrix). As such, when multiple fibers (fibrils) are bioprinted to form a layer, those fibers can be deposited in parallel form to form at least one layer that forms the bioscaffold. It can be even more beneficial to have a random arrangement of the printed fibers to produce a random arrangement of pore structures across the layer. Moreover, even if a layer includes parallel deposited fibers, subsequent overlaid layers can include the random arrangement of printed fibers to produce the random arrangement of pore structures across multiple layers and, by extension, across the entire bioscaffold structure. Fibers can be printed, therefore, in a raster pattern with raster angles between about 10 and about 90 degree orientations relative to each other (also referred to as angular range) to produce a random pore arrangement. Moreover, fibers can be printed to form pores between about 100 to about 500 microns across the multiple layers of the bioscaffold structure. In various embodiments, the pore size can be about 50 microns to about 1000 microns, or about 50 microns to about 500 microns, or about 100 microns to about 1000 microns.

Moreover, unit cell geometries can be the same across the matrix, can include a specific defined group of alternating geometries, or can be entirely random. While each type of unit cell geometry distribution can provide the requisite infiltration, cellular attachment, and tissue remodeling or regeneration profile, a distribution of random or specifically varied unit cell geometries can provide even more beneficial infiltration, attachment and remodeling/regeneration. Moreover, even if a consistent unit cell geometry is applied across a matrix, a random orientation of the unit cells can provide similar beneficial characteristics. As shown in FIG. 1d, for example, while unit cell geometries may be the same, the random orientation of the unit cells in relation to each other across a multi-layer matrix can provide the beneficial characteristics described above.

As relating the structural integrity, in accordance with various embodiments, structural properties can include, for example, tensile strength, stiffness, max load, tensile stress, tensile strain (a ratio of the extension and original length of the bioscaffold structure), and modulus of elasticity. The bioscaffold structure can have a tensile strength of between about 10 Newtons per centimeter (N/cm) to about 200 N/cm. Further, the bioscaffold structure can have a tensile strength of between about 30 N/cm to about 100 N/cm. Preferably, the bioscaffold structure can have a tensile strength of between about 50 N/cm to about 85 N/cm.

In accordance with various embodiments, the bioscaffold structure can have a tensile stress limit of about 3 megapascals (MPa) to about 100 MPa. Preferably, the bioscaffold structure can have a tensile stress limit of about 10 MPa to about 30 MPa.

In accordance with various embodiments, the bioscaffold structure can further have a tensile strain limit of greater than about 10%. Further, the bioscaffold structure can further have a tensile strain limit of greater than about 35%. Preferably, the bioscaffold structure can further have a tensile strain from about 20% to about 80%.

In accordance with various embodiments, the bioscaffold structure can have a stiffness of less than about 80 N/mm. Further, the bioscaffold structure can have a stiffness of less than about 18 N/mm. Preferably, the bioscaffold structure can have a stiffness greater than about 5 N/mm and less than about 18 N/mm.

In accordance with various embodiments, the bioscaffold structure can have a maximum load of greater than about 50N. Further, the bioscaffold structure can have a maximum load of greater than about 150N. Preferably, the bioscaffold structure can have a maximum load of greater than about 150N and less than about 400 N.

In accordance with various embodiments, the bioscaffold structure can have a modulus of elasticity of from about 10 MPa to about 450 MPa. Further, the bioscaffold structure can have a modulus of elasticity of less than about 150 MPa. Preferably, the bioscaffold structure can have a modulus of elasticity of from about 60 MPa to about 150 MPa.

It should be appreciated that the extracellular material of the bioscaffold structure, which can include polycaprolactone (PCL) and/or another dissolvable or liquefiable polymer, as well as the subsequent layering of that polymer, can aid in providing the structural integrity and function (e.g., suturing and expansion) of the bioscaffold structure as well as the unit cells that make up the structure.

In accordance with various embodiments, a bioscaffold structure is provided. The structure can comprise a layer of fibers (fibrils) composed of an extracellular material containing Collagen I and Collagen III. The layer can include a plurality of pores. The plurality of pores can have diameters that are substantially equal, or in the alternative, be random across the bioscaffold structure. In various embodiment, the plurality of pores can have a diameter of between about 100 microns to about 500 microns. Alternatively, at least one of the pores can be a shape other circular, wherein the at least one pore can have a length of between about 100 microns to about 500 microns, or about 50 microns to about 1000 microns, or between about 50 microns to about 500 microns, or about 100 microns to about 1000 microns. In various embodiments, each fiber (fibril) of the bioscaffold structure can have a diameter of at least about 100 microns.

The extracellular material of the bioscaffold structure can contain a Collagen I to Collagen III ratio similar to those contained within fetal and adolescent dermis. Current tissue offerings, which are predominantly taken from adult and elderly donors, contain much higher ratios of Collagen I to Collagen III, thereby providing decreased support, cushioning, protection, reinforcement and covering than do tissues containing lower ratios. The extracellular material of the bioscaffold structure can contain a Collagen I to Collagen III ratio similar to those contained within human dermis (e.g., fetal, adolescent, adult and elderly) as shown in Table I above.

That is, in various embodiments, the extracellular material can have a Collagen I to Collagen III ratio in the range of between about 0.5 to about 3.5, or in the range of between about 0.75 to about 3.0, or in the preferred range of between about 0.9 to about 2.5. The preferred Collagen I to Collagen III ratio range of between about 0.9 to about 2.5 may offer advantages against conventional tissue offerings, which are predominantly taken from adult and elderly donors (contain much higher ratios of Collagen I to Collagen III) thereby providing decreased support, cushioning, protection, reinforcement and covering than do tissues containing lower ratios.

More specific ratios of Collagen I to Collagen III can include about 0.5, about 0.55, about 0.6, about 0.65, about 0.7, about 0.75, about 0.8, about 0.85, about 0.9, about 0.95, about 1.0, about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 1.95, about 2.0, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3.0, about 3.05, about 3.1, about 3.15, about 3.2, about 3.25, about 3.3, about 2.35, about 3.4, about 3.45, about 3.5 and ranges between any two of these values.

Collagen I and Collagen III can help provide a platform for infiltrating cells to attach to the bioscaffold structure, by providing an extensive network of extracellular matrix cues that provide an appropriate cell niche for host cell receptor recognition, in-growth, vascularization and remodeling within the breast, other organs, or other anatomy and surrounding tissues currently unattainable in synthetic matrix offerings. Collagen I and Collagen III also aide in directing cell fate and differentiation. Identification of these collagen components by cell surface receptors induce the production of signaling molecules needed for tissue generation and scaffold remodeling.

The extracellular material can comprise further bioactive materials. These bioactive molecules can include, but are not limited to, other types of collagen (e.g., Collagen II, Collagen IV, Collagen V, etc.), extracellular matrix proteins (such as elastin, glycosaminoglycans (GAGs), laminin, fibronectin, etc.), growth factors, cytokines, polysaccharides, selected cell populations, small molecules and small molecule inhibitors, antibiotics, antimicrobials, nanoparticles, mesoporous silica, silk fibroin, enzymatic degradation sites, and any combination thereof. Anti-fibrotic agents can be included in the extracellular material, with examples such as anti-transforming growth factor beta (anti-TGF-β) and anti-tumor necrosis factor alpha (anti-TNF-α). Pro-angiogenic agents can be included in the extracellular material, with examples such as vascular endothelial growth factor (VEGF) and placental growth factor (PlGF). Factors affecting adipogenesis and proliferation can be included in the extracellular material, with examples such as insulin-like growth factor 1 (IGF-1) and Dexamethasone.

The plurality of pores can have a diameter of between about 100 microns to about 500 microns. Alternatively, the plurality of pores can be a shape other than circular, wherein the at least one opening can have a length of between about 100 microns to about 500 microns, or about 50 microns to about 1000 microns, or between about 50 microns to about 500 microns, or about 100 microns to about 1000 microns. Each fiber (fibril) of the bioscaffold structure can have a diameter of less than or equal to about 100 microns.

As discussed above, in order to sufficiently promote appropriate tissue ingrowth, the size of the pores, as well as their orientation in relation to each other and their geometry, will be critical. Pores should be large enough to accommodate the size and geometry of the infiltrating cell, but small enough so that infiltrating cells can attach not only to a bioscaffold structure, but to each other as well, to form complex interconnected cellular signaling networks, allowing for scaffold degradation, collagen synthesis and tissue regeneration. As such, the material can be "spongy" enough to allow cellular infiltration throughout the entire construct (length, width, height and depth). For example, as applied to human skin, human dermal fibroblasts are typically approximately 30-70 microns in width. Therefore, it was determined that a pore size from about 100 microns to about 500 microns will allow cellular infiltration, while still providing a niche in which cells are able to communicate via membrane or cytokine signaling.

The extracellular material of the bioscaffold structure can also contain a polymer. The polymer can be a dissolvable or liquefiable polymer. The polymer can be natural or synthetic. Examples of polymers include polyethylene glycol (PEG), Poly(lactide-co-clycolide) (PLGA), polycaprolactone (PCL), poly(l-lactic acid (PLLA), ethylene propylene, polyethylene terephthalate, alginate, hyaluronic acid, gelatin, soy protein, fibrinogen, chitosan, dextran, starch or another type of polymer. In various embodiments, the polymer can be polycaprolactone.

The layer of the bioscaffold structure can form part of a substantially planar sheet as shown in FIG. 2. The layer of the bioscaffold structure can form part of a 3D macrostructure as shown in FIGS. 3 and 4. The layer of the bioscaffold structure can have a thickness of between about between about 0.5 mm to about 200 mm, or between about 0.5 mm to about 20 mm, or between about 0.5 mm to about 2.5 mm. The 3D macrostructure can include, for example, a "hand in glove" fit configuration (FIG. 3) and a "ready-to-use" solid implant configuration (FIG. 4) discussed in more detail below.

Similar to that discussed above, the specific geometries of the unit cells (made up of groups of filaments) can correlate to the size and arrangement of the bioprinted filaments that make up the unit cell, as well as the arrangement of the openings (pores) and the opening size (pore size) created by material deposition (the material deposition process discussed in more detail below). Cellular fate and function can be dictated by the fiber size, pore size of the overall matrix (e.g., individual planar and non-planar sheet, or plurality of sheets, that make up the implant), matrix density/height, base polymer (if used), extracellular material composition, and the use/interplay between a standardized pore structure (e.g., of the overall matrix) and/or the random arrangement of pore structures (e.g., of the overall matrix). As such, when multiple fibers are bioprinted to form a layer, those fibers can be deposited in parallel form to form at least one layer that forms the bioscaffold. It can be even more beneficial to have a random arrangement of the printed fibers to produce a random arrangement of pore structures across the layer. Moreover, even if a layer includes parallel deposited fibers, subsequent overlaid layers can include the random arrangement of printed fibers to produce a random arrangement of pore structures across multiple layers and, by extension, across the entire bioscaffold structure. Fibers can be printed, therefore, in a raster pattern with raster angles between about 10 and about 90 degree orientations relative to each other (also referred to as angular range) to produce a random pore arrangement. Moreover, fibers can be printed to form pores between about 100 to about 500 microns across the multiple layers of the bioscaffold structure. See below for further discussion related to manufacturing processes of the bioscaffold structure.

Moreover, as discussed above, unit cell geometries can be the same across the matrix, can include a specific defined group of alternating geometries, or can be entirely random. While each type of unit cell geometry distribution can provide the requisite infiltration, cellular attachment, and tissue remodeling or regeneration profile, a distribution of random or specifically varied unit cell geometries can provide even more beneficial infiltration, attachment and remodeling/regeneration. Moreover, even if a consistent unit cell geometry is applied across a matrix, a random orientation of the unit cells can provide similar beneficial characteristics. As shown in FIG. 1d, for example, while unit cell geometries may be the same, the random orientation of the unit cells in relation to each other across a multi-layer matrix can provide the beneficial characteristics described above.

As relating the structural integrity, in accordance with various embodiments, structural properties of the bioscaffold structure, or layer of the bioscaffold structure, can include, for example, tensile strength, stiffness, max load, tensile stress, tensile strain, and modulus of elasticity. The layer of the bioscaffold structure can have a tensile strength of between about 10 Newtons per centimeter (N/cm) to about 200 N/cm. Further, the layer of the bioscaffold structure can have a tensile strength of between about 30 N/cm to about 100 N/cm. Preferably, the layer of the bioscaffold structure can have a tensile strength of between about 50 N/cm to about 85 N/cm.

In accordance with various embodiments, the layer of the bioscaffold structure can have a tensile stress limit of about 3 megapascals (MPa) to about 100 MPa. Preferably, the layer of the bioscaffold structure can have a tensile stress limit of about 10 MPa to about 30 MPa.

In accordance with various embodiments, the layer of the bioscaffold structure can further have a tensile strain limit of greater than about 10%. Further, the layer of the bioscaffold structure can further have a tensile strain limit of greater than about 35%. Preferably, the layer of the bioscaffold structure can further have a tensile strain from about 20% to about 80%.

In accordance with various embodiments, the layer of the bioscaffold structure can have a stiffness of less than about 80 N/mm. Further, the layer of the bioscaffold structure can have a stiffness of less than about 18 N/mm. Preferably, the layer of the bioscaffold structure can have a stiffness greater than about 5 N/mm and less than about 18 N/mm.

In accordance with various embodiments, the layer of the bioscaffold structure can have a maximum load of greater than about 50N. Further, the layer of the bioscaffold structure can have a maximum load of greater than about 150N. Preferably, the layer of the bioscaffold structure can have a maximum load of greater than about 150N and less than about 400 N.

In accordance with various embodiments, the layer of the bioscaffold structure can have a modulus of elasticity of from about 10 MPa to about 450 MPa. Further, the layer of the bioscaffold structure can have a modulus of elasticity of less than about 150 MPa. Preferably, the layer of the bioscaffold structure can have a modulus of elasticity of from about 60 MPa to about 150 MPa.

As stated above, the extracellular material of the bioscaffold structure, which can include polycaprolactone (PCL) and/or another dissolvable or liquefiable polymer, as well as the subsequent layering of that polymer, can aid in providing the structural integrity and function (e.g., suturing and expansion) of the bioscaffold structure as well as the unit cells that make up the structure.

In accordance with various embodiments, the bioscaffold structure can take many forms including, for example, membranes, microbeads, fleece, fibers, gels and fiber meshes. A finished product mesh, for example, implementing the bioscaffold structure in accordance with various embodiments herein, can provide the requisite porosity to allow optimal cellular infiltration and provide a large enough niche for cells to attach, and ultimately direct cell fate towards a remodeling/regenerative phenotype rather than fibrotic/contractile phenotype. Furthermore, from a mechanical/structural perspective, the arrangement of the scaffold structure provides the appropriate mechanical strength and elasticity to be physiologically relevant as well as useful as a supportive matrix. These features can be provided by the bioscaffold structure using, for example, an optimal extracellular material composition, as discussed previously, thereby providing the necessary structural integrity properties as also discussed previously. Determining the optimal composition to provide the requisite integrity can be accomplished by systemically varying, for example, pore size, angular filament deposition range, density, height, polymer type and filament size (e.g., diameter).

In accordance with various embodiments, and as provided by way of example in FIG. 2, a final tissue construct can be, for example, a flat sheet that is two-dimensional (2D). As provided by way of example in FIG. 3, another and more advanced final tissue construct can be, for example, molded sheets/constructs that provide a "hand in glove fit" for tissue reinforcement, to hold breast implants or other medical devices, anatomy or physiology within the breast (e.g., breast pocket), other organs, or other anatomy. As provided by way of example in FIG. 4, yet another advanced final tissue construct can be, for example, a "ready-to-use" lumpectomy defect implant within the breast (e.g., breast pocket), other organs, or other anatomy. The solid, implant-style construct (see FIG. 4) can be printed, for example, from a range of from about 20 g to about 4500 g sizes for breast applications (e.g., lumpectomy) or custom sized for other anatomic applications. For example, the implant can be a prolate spheroid shaped (i.e. football) (see FIG. 4), custom shaped, or shaped in another pre-determined geometrical configuration.

Such final tissue constructs can advantageously provide improved ease of use during the implant procedure by minimizing intraoperative manipulation while improve procedural efficiency for patients. For example, a three-dimensional (3D) construct, in accordance with various embodiments, would provide patients with a "ready-to-use" implant option, improving procedural efficiency for physicians and patients in the areas of, for example, tissue reinforcement and lumpectomy implants. By contrast, current cadaveric acellular dermal matrix (ADM) offerings are supplied as two-dimensional (2D) sheets of tissue, requiring extensive manipulation of the tissue sheet necessitating the surgeon to sew (or bind or connect) the acellular dermal matrix sheet into a pouch-like structure prior to implantation to create an adequate 3D pocket for a breast implant or tissue reinforcement application. This extensive manipulation requires additional procedure time and can introduce potential contamination.

Moreover, ADMs are hampered by tissue quality (due to age, smoking history, drug use), varied national regulatory constraints, donor availability, donor matching, host immune status, cost, and so on. By contrast, bioprinted scaffolds, in accordance with various embodiments herein, advantageously eliminates issues of donor availability, variability and quality/health status, tissue quality and regulatory policies. Moreover, by being bioprinted using controlled parameters of the scaffold to meet required properties of the end product, the bioprinted scaffolds allow for personalized medical applications that ADMs simply do not. These personalized medical applications include, for example but not limited to, lumpectomies (as discussed above), tubular cartilage applications, valvular heart disease applications, and coronary artery disease applications, hernia repair applications, tissue graft applications, venous, arterial and lymphatic vessel applications, structural applications or supportive applications where soft tissue defects exist.

With regards to tissue reinforcement, the uses and advantages of a biologic acellular dermal matrix, in accordance with various embodiments, are varied and substantial. One exemplary use is pectoralis muscle reattachment by allowing for greater initial tissue expander fill volume for a two stage breast reconstruction or implant placement for a single stage breast reconstruction. Another exemplary use is implant position maintenance (support) by helping to define the shape of the breast pocket by defining the inframammary fold, supporting the implant in a pre-pectoral breast reconstruction, and correcting implant malposition such as symmastia, bottoming out, etc. Another exemplary use is aesthetic defect camouflaging by using the scaffold as a buffer or a means to thicken tissue to mask unwanted cosmetic outcomes such as rippling. Other exemplary uses and benefits are capsular contracture reduction and more positive tissue response during radiation treatments.

The unique combination components (i.e., polymer and bioactive materials such as Collagen I and III), in accordance with various embodiments, together in the construct provide the appropriate support matrix for remodeling. The combination of the polymeric and biologic construct materials also provides a robust scaffold for the addition of other bioactive materials, as discussed above, to elicit specific host responses to enhance recovery, minimize undesired complications, and promote further vascularization, remodeling and host-cell ingrowth. Further, the construct can minimize host immunogenic response by containing known and desired components (to include the use of the aforementioned synthetic, protein, molecular or other components) thus minimizing non-specific immune responses.

By contrast, currently available offerings, while devoid of cellular material, may contain molecular moieties (unbeknownst to surgeons), which may prove deleterious to the healing process and trigger am immunogenic response, or "graft vs. host response". By controlling the combination of components in the scaffold to provide specific physical properties and implant outcomes, the construct, in accordance with the various embodiments herein, eliminates immunogenic response concerns, and will allow for the standardization of clinical outcomes within and among patients.

Additionally, currently available tissue offerings may have inconsistent surface topography throughout. In the case of woven, spun or knitted synthetic constructs, the lack of appropriate microarchitecture affects the ability of host cells to recognize the graft as self, and promote cell adhesion, and thus inhibit a robust regenerative response. By controlling the combination of components in the scaffold to provide specific physical properties and implant outcomes, in accordance with the various embodiments herein, the construct will have consistent surface topography throughout with an engineered microarchitecture (controlling microarchitecture properties such as, for example, porosity, fiber diameter, spacing, height of matrix, fiber orientation, etc.) that provides the appropriate scaffold for a robust wound healing, regenerative, infiltrative and remodeling response.

Moreover, the construct will provide, for example, cushioning and structural support for other tissues, supplemental support, protection, reinforcement and covering within the breast, other organs, or other anatomy and surrounding tissue, while stimulating host cell remodeling. The construct will allow, for example, plastic and reconstructive surgeons to support, repair, elevate and reinforce deficiencies where weakness or voids exist in, for example, the breast, other organs, or other anatomy and surrounding tissue that requires the addition of material to obtain the desired surgical outcome. Furthermore, the construct will allow for the repair of fascial defects within the breast, other organs, or other anatomy and surrounding tissues that require the addition of a reinforcing or bridging material to obtain a desired surgical result.

Additive manufacturing processes, such as, for example, 3D printing manufacturing methods, allow for control of the macro (overall finished shape) and micro (cell units) structure of the construct, and will be discussed in detail below. The manufacturing process of 3D bioprinting, for example, allows for the flexible and accurate production of all final product tissue construct configurations, without the limitation of traditional manufacturing limitations such as tool access, allowing for ultimate design freedom of the complex unit cell geometries needed.

In summary, the construct will minimize concerns over donor availability, alleviate increasing costs, be a possible solution for non-U.S. regulatory restrictions and eliminate concerns over tissue quality, variability, immunogenicity and the potential for contamination. The simplicity of the product would not add additional complexity to the procedure. Instead, it would seamlessly replace existing technologies in the current surgical technique. As the surgical principals of breast, organ and tissue reconstruction continue to evolve into novel surgical planes, and approaches for unique patient populations and needs, the need for a 3D, anatomically accurate, ECM product has never been more important.

Manufacturing Processes

The porous three-dimensional extracellular structures or bioscaffold structures discussed above can be made using a variety of different additive manufacturing techniques, which are processes involving the use of digital 3D design data to build up an extracellular construct in layers by depositing successive layers of extracellular material. Additive manufacturing processes can include, for example, material jetting (or ink jet) 3D printing, extrusion 3D printing, fused deposition 3D printing, liquid material 3D printing, melt electrospinning, and so on. Additive manufacturing processes offer some unique advantages over other extracellular component manufacturing techniques with respect to the manufacture of porous three-dimensional extracellular structures (disclosed above) due to the complexities of the geometries and structural elements of the unit cells which comprise those types of structures.

Figure 5:
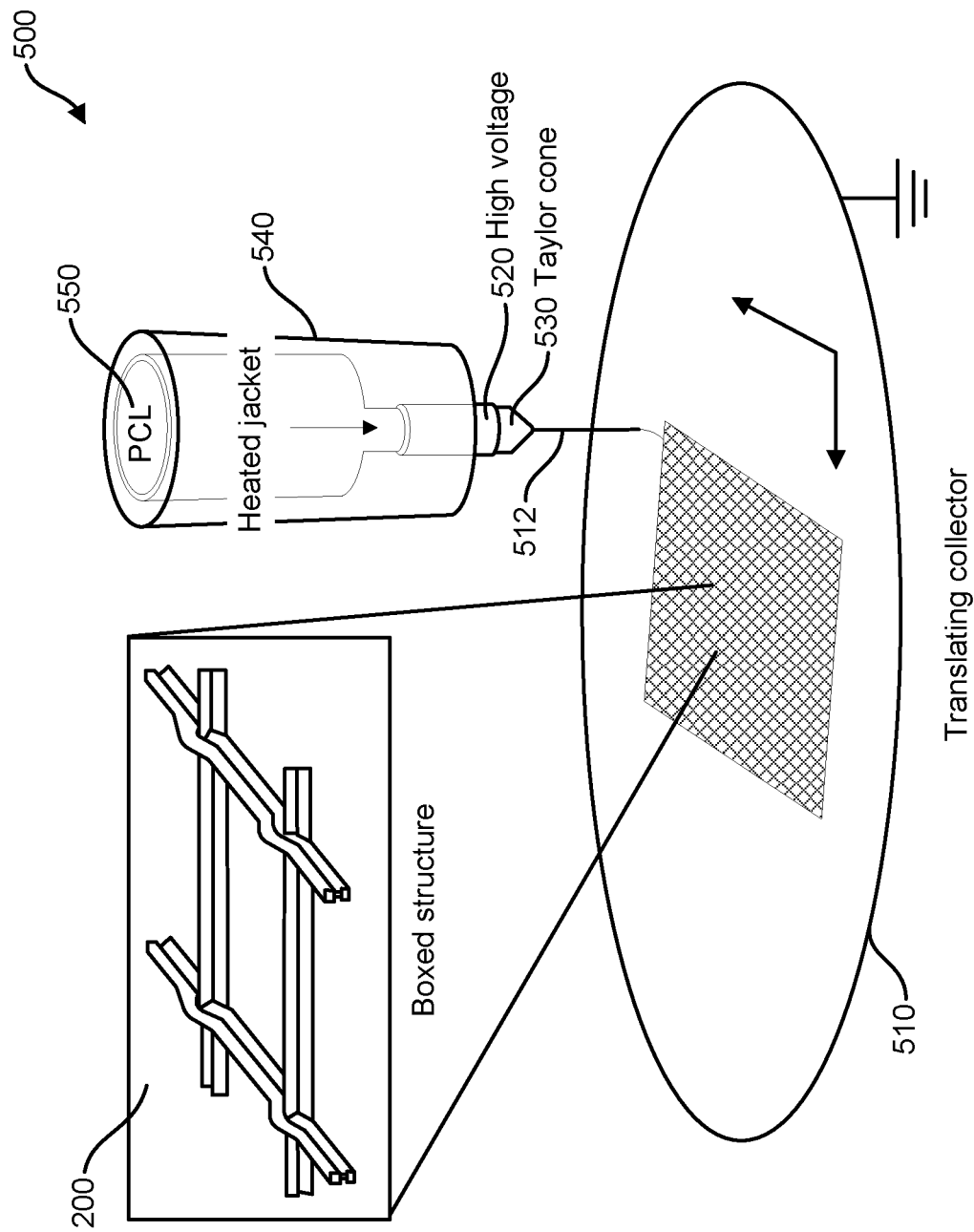
FIG. 5 illustrates a melt electrospinning based manufacturing process for producing a bioscaffold structure, in accordance with various embodiments.
Figure 8:
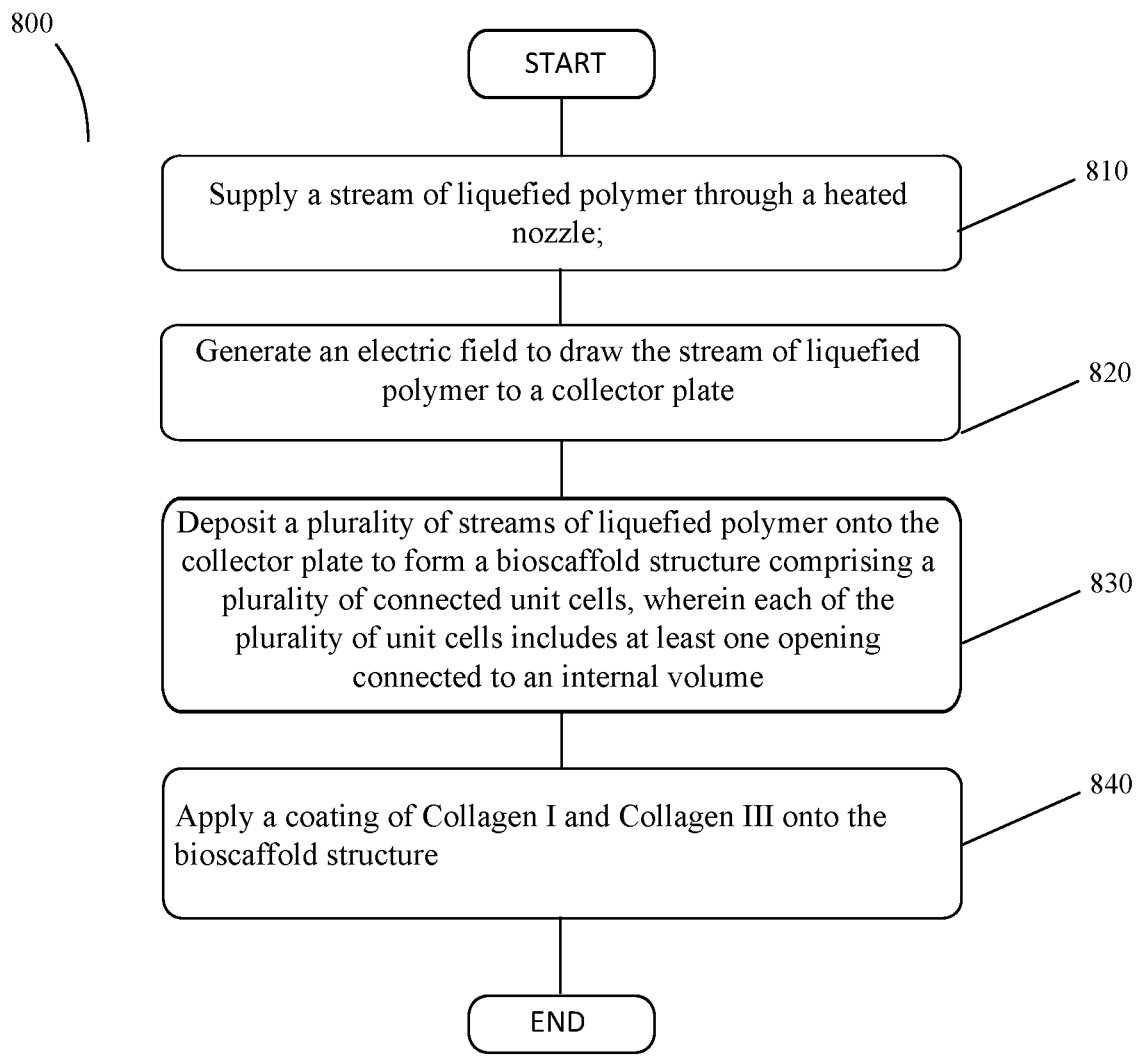
FIG. 8 is a flowchart illustrating a process for producing a bioscaffold structure, in accordance with various embodiments.

In accordance with various embodiments, a method for producing a bioscaffold structure is provided as illustrated, for example, in FIG. 5, by method 800 of FIG. 8. As provided in FIG. 8, method 800 can comprise, at step 810, supplying a stream of liquefied polymer (i.e., PCL) through a heated nozzle. In various embodiments, the liquefied polymer is comprised of a solution or mixture containing one or more polymer components. In various embodiments, the liquefied polymer is comprised of a polymer material that has been heated beyond its melting point to a fluid state. Method 800 can further comprise, at step 820, generating an electric field to draw the stream of liquefied polymer to a collector plate. In various embodiments, the electric field is created by generating a high potential difference (voltage) between the nozzle head (spinneret) supplying the liquefied polymer and the collector plate. In step 830, a plurality of streams of liquefied polymer is deposited onto the collector plate to form a bioscaffold structure comprising a plurality of connected unit cells, wherein each of the plurality of unit cells includes at least one opening connected to an internal volume (as depicted in FIGS. 1*a* and 1*e*). In various embodiments, steps 810 and 820 are repeated such that a plurality of streams of liquefied polymer are successively deposited on top of each other to form the bioscaffold structure. In various embodiments, the strength of the electric field (and thus the voltage applied) generated is increased with each successive layer of polymer that is deposited and/or with the thickness of the bioscaffold structure.

In step 840, a coating of collagen (e.g., Collagen I, Collagen II, Collagen III, Collagen IV, Collagen V, etc.) is applied onto the bioscaffold. In various embodiments, the applied collagen coating is deposited on the external surfaces (i.e., outside surfaces) and internal surfaces (e.g., pores, pore volume surfaces, etc.) of the bioscaffold structure.

In various embodiments, the collagen coating includes Collagen I and Collagen III. In various embodiments, the collagen coating can contain a Collagen I to Collagen III ratio similar to that contained within human fetal and adolescent dermis. Conventional tissue offerings, which are predominantly taken from adult and elderly donors, contain a higher ratio (i.e., greater than about 2.4) of Collagen I to Collagen III, thereby providing decreased support, cushioning, protection, reinforcement and covering than do tissues containing lower ratios.

In various embodiments, the collagen coating can have a Collagen I to Collagen III ratio in the range of between about 0.5 to about 3.5, or in the range of between about 0.75 to about 3.0, or in the preferred range of between about 0.9 to about 2.5. The preferred Collagen I to Collagen III ratio range of between about 0.9 to about 2.5 may offer advantages against conventional tissue offerings, which are predominantly taken from adult and elderly donors, contain much higher ratios of Collagen I to Collagen III, thereby providing decreased support, cushioning, protection, reinforcement and covering than do tissues containing lower ratios.

More specific ratios of Collagen I to Collagen III can include about 0.5, about 0.55, about 0.6, about 0.65, about 0.7, about 0.75, about 0.8, about 0.85, about 0.9, about 0.95, about 1.0, about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 1.95, about 2.0, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3.0, about 3.05, about 3.1, about 3.15, about 3.2, about 3.25, about 3.3, about 2.35, about 3.4, about 3.45, about 3.5 and ranges between any two of these values.

In various embodiments, the collagen (e.g., Collagen I, Collagen II, Collagen III, Collagen IV, Collagen V, etc.) and/or other ECM materials can be combined with the liquefied polymer to form a bioink that can be deposited to form the bioscaffold structure in a single process step instead of successive process steps.

In various embodiments, the collagen and/or ECM material coating can be lypholized to sublime the solvent used to create the suspension thus allowing the collagen and/or ECM material coating to adhere to the bioscaffold structure.

In various embodiments, the bioscaffold structure can be scanned with an electron beam, UV light or chemical agent such as EDAC, carbodiimide (or other physical or chemical crosslinker prior to the application of the collagen and/or ECM material coating in order to crosslink the polymers and increase the structural strength and integrity of the bioscaffold structure.

As illustrated in FIG. 5, a stream of liquefied polymer 512 can be deposited, via a nozzle (spinneret) 520, onto a collector plate 510. A heating element (jacket) 540 can be used to raise the temperature of a solid or semi-solid polymer material 550 beyond its melting point to a fluid state to form a liquefied polymer. A stream of liquefied polymer can be drawn out of the nozzle 530 by an electric field generated by a high voltage element 520. The stream of liquefied polymer 512 can form a single or multiple layer(s) comprised of a plurality of unit cell structures 200. The depositing process can be repeated to add additional layers to increase the thickness of the liquefied polymer deposition until a desired thickness is achieved for a finished product. The finished product can be, as discussed above, a substantially planar sheet or a 3D macrostructure. The 3D macrostructure can include, for example, a "hand in glove" fit configuration and a "ready-to-use" solid implant configuration discussed in more detail above.

Figure 6:
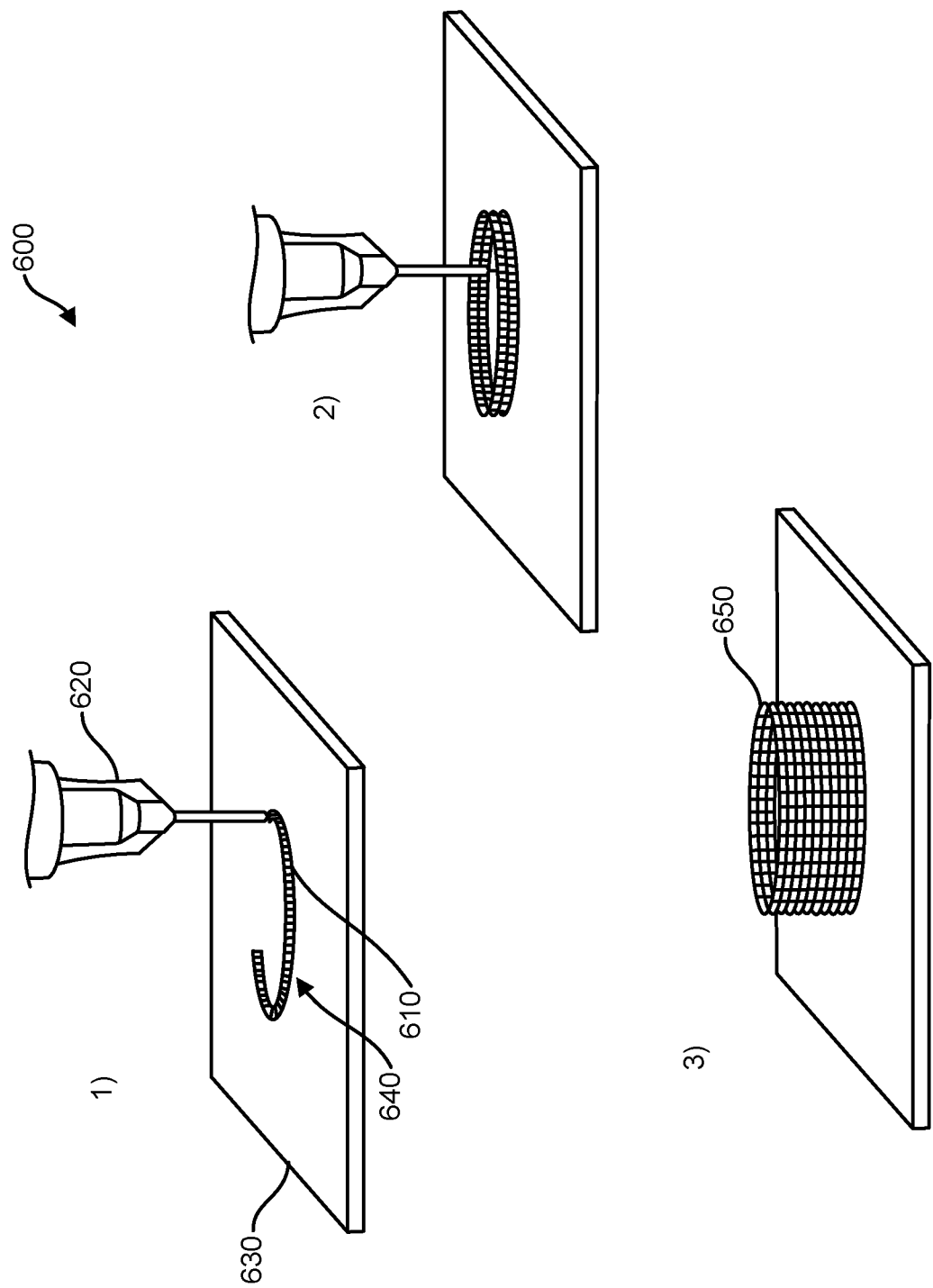
FIG. 6 illustrates a fused deposition modeling manufacturing process for producing a bioscaffold structure, in accordance with various embodiments.
Figure 9:
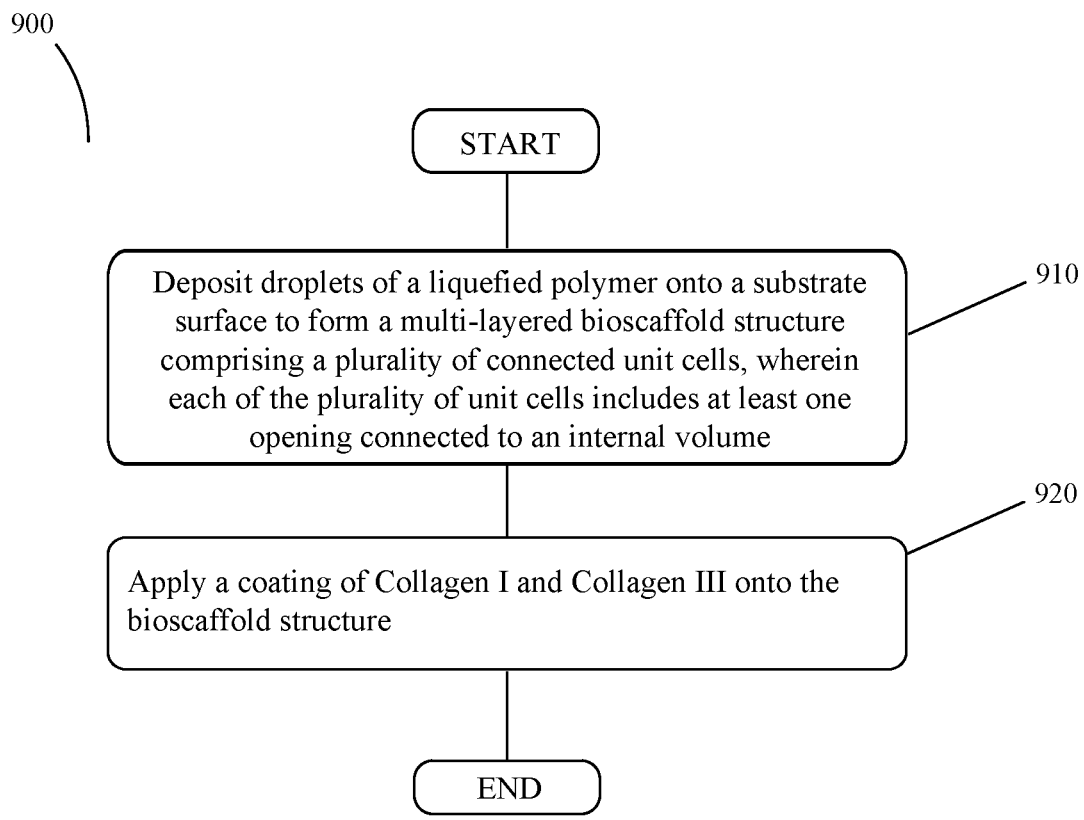
FIG. 9 is a flowchart illustrating a process for producing a bioscaffold structure, in accordance with various embodiments.

In accordance with various embodiments, a method for producing a bioscaffold structure is provided as illustrated in FIG. 6 and provided by method 900 of FIG. 9. As provided in FIG. 9, method 900 can comprise, at step 910, depositing droplets of a liquefied polymer onto a substrate surface to form a bioscaffold structure comprising a plurality of connected unit cells, wherein each of the plurality of unit cells includes at least one opening connected to an internal volume. In various embodiments, the liquefied polymer is comprised of a solution or mixture containing one or more polymer components. In various embodiments, the liquefied polymer is comprised of a polymer material that has been heated beyond its melting point to a fluid state.

In various embodiments, step 910 can be repeated such that the drops of liquefied polymer are successively deposited on top of each other to form the bioscaffold structure.

Method 900 further comprises, at step 920, applying a collagen (e.g., Collagen I, Collagen II, Collagen III, Collagen IV, Collagen V, etc.) coating onto the bioscaffold structure. In various embodiments, the applied collagen coating is deposited on the external surfaces (i.e., outside surfaces) and internal surfaces (e.g., pores, pore volume surfaces, etc.) of the bioscaffold structure.

In various embodiments, the collagen coating includes Collagen I and Collagen III. In various embodiments, the collagen coating can contain a Collagen I to Collagen III ratio similar to those contained within fetal and adolescent dermis. Current tissue offerings, which are predominantly taken from adult and elderly donors, contain much higher ratios of Collagen I to Collagen III, thereby providing decreased support, cushioning, protection, reinforcement and covering than do tissues containing lower ratios.

In various embodiments, the collagen coating can have a Collagen I to Collagen III ratio in the range of between about 0.5 to about 3.5, or in the range of between about 0.75 to about 3.0, or in the preferred range of between about 0.9 to about 2.5. The preferred Collagen I to Collagen III ratio range of between about 0.9 to about 2.5 may offer advantages against conventional tissue offerings, which are predominantly taken from adult and elderly donors, contain much higher ratios of Collagen I to Collagen III, thereby providing decreased support, cushioning, protection, reinforcement and covering than do tissues containing lower ratios.

More specific ratios of Collagen I to Collagen III can include about 0.5, about 0.55, about 0.6, about 0.65, about 0.7, about 0.75, about 0.8, about 0.85, about 0.9, about 0.95, about 1.0, about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 1.95, about 2.0, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3.0, about 3.05, about 3.1, about 3.15, about 3.2, about 3.25, about 3.3, about 2.35, about 3.4, about 3.45, about 3.5 and ranges between any two of these values.

In various embodiments, the collagen (e.g., Collagen I, Collagen II, Collagen III, Collagen IV, Collagen V, etc.) and/or other ECM materials can be combined with the liquefied polymer to form a bioink that can be deposited to form the bioscaffold structure in a single process step instead of successive process steps.

In various embodiments, the collagen and/or ECM material coating can be lypholized to sublime the solvent used to create the suspension thus allowing the collagen and/or ECM material coating to adhere to the bioscaffold structure.

In various embodiments, the bioscaffold structure can be scanned with an electron beam, UV light or chemical agent such as EDAC, carbodiimide (or other physical or chemical crosslinker prior to the application of the collagen and/or ECM material coating in order to crosslink the polymers and increase the structural strength and integrity of the bioscaffold structure.

In various embodiments, the at least one opening of each of the plurality of unit cells can have a diameter of between about 100 microns to about 500 microns. Moreover, each of the plurality of unit cells can comprise filaments that have a diameter of less than or equal to about 100 microns. The plurality of connected unit cells can also form a substantially planar sheet. Further, the plurality of connected unit cells can form a 3D macrostructure. The 3D macrostructure can include, for example, a "hand in glove" fit configuration and a "ready-to-use" solid implant configuration discussed in more detail above.

As illustrated in FIG. 6, step (1), liquefied polymer droplets 610 can be deposited, via syringe or nozzle (or any other deposition device) 620, onto a substrate 630. Droplets 610 can form a single layer 640. As shown in step (2), the depositing process can be repeated to add additional liquefied polymer layers to increase the thickness of the liquefied polymer deposition until a desired thickness is achieved for a finished product 650, as provided in step (3). The droplets of liquefied polymer can form a single or multiple layer(s) comprised of a plurality of unit cell structures. The finished product can be, as discussed above, a substantially planar sheet or a 3D macrostructure. The 3D macrostructure can include, for example, a "hand in glove" fit configuration and a "ready-to-use" solid implant configuration discussed in more detail above.

Each unit cell of the bioscaffold structure can comprise a polymer with a collagen coating. The polymer can be polycaprolactone. The composition that is deposited can be in the form of a slurry of polymer with the Collagen I/Collagen III embedded, mixed, or encapsulated with the polymer. Alternatively, the droplets of Collagen I/Collagen III and droplets of liquefied polymer can be deposited separately and then interlaced to form the structure. The deposition can be performed, for example, by a bioprinter using components such as, for example, a nozzle or syringe. These components can be, for example, pneumatically, piston, or screw driven. Pneumatic driven syringes, for example, can deposit liquefied polymer in sequential layers to create the construct, which will ultimately be crosslinked. Bioactive molecules (e.g., Collagen I/Collagen III based bioinks with any other additional bioactive components as discussed above) can either be co-printed along with the base polymer or layered upon the base polymer layer sequentially.

As compared to traditional polymer-based compositions, which can be deposited via additive manufacturing techniques under heated conditions and relatively higher pressures to promote scaffold formation while still maintaining structural stability of the polymer-based composition, certain bioinks containing bioactive molecules in addition to polymer may have to be deposited under milder conditions relative to polymer-based compositions. This can be due to the relatively more delicate nature of bioink structures (e.g., higher water content, non-crystalline structure, etc.). As such, bioprinting process parameters such as printing pressure or nozzle/syringe diameter can be considered in reducing the shear stress on some bioinks to prevent damaged or lysed cells, which can affect cell viability in the bioinks. Other parameters that may be considered, and correspondingly controlled include, for example, printing temperature (e.g., lower temperature than polymer-based compositions), uniformity in diameter of the filaments that make up the unit cell, angles at the interaction of filaments, bleeding of filaments together at intersects, and maintenance of shape fidelity after printing but before cross-linking with polymer-based compositions. Therefore, and in accordance with various embodiments, the polymer and bioactive molecules (e.g., Collagen I/Collagen III and any other additional bioactive components as discussed above) can be deposited as, for example, droplets or streams (see below for more detail) separately utilizing separately defined process parameters to ensure scaffold manufacturing while maintaining structural integrity of each respective deposited compositions. The deposition of the polymers and bioactive molecules (e.g., Collagen I/Collagen III and any other additional bioactive components as discussed above) can occur, as stated above, separately and then interlaced or crosslinked to form the scaffold. To accomplish this, the bioactive molecules can either be co-printed along with the base polymer or layered upon the base polymer layer sequentially.

Figure 7:
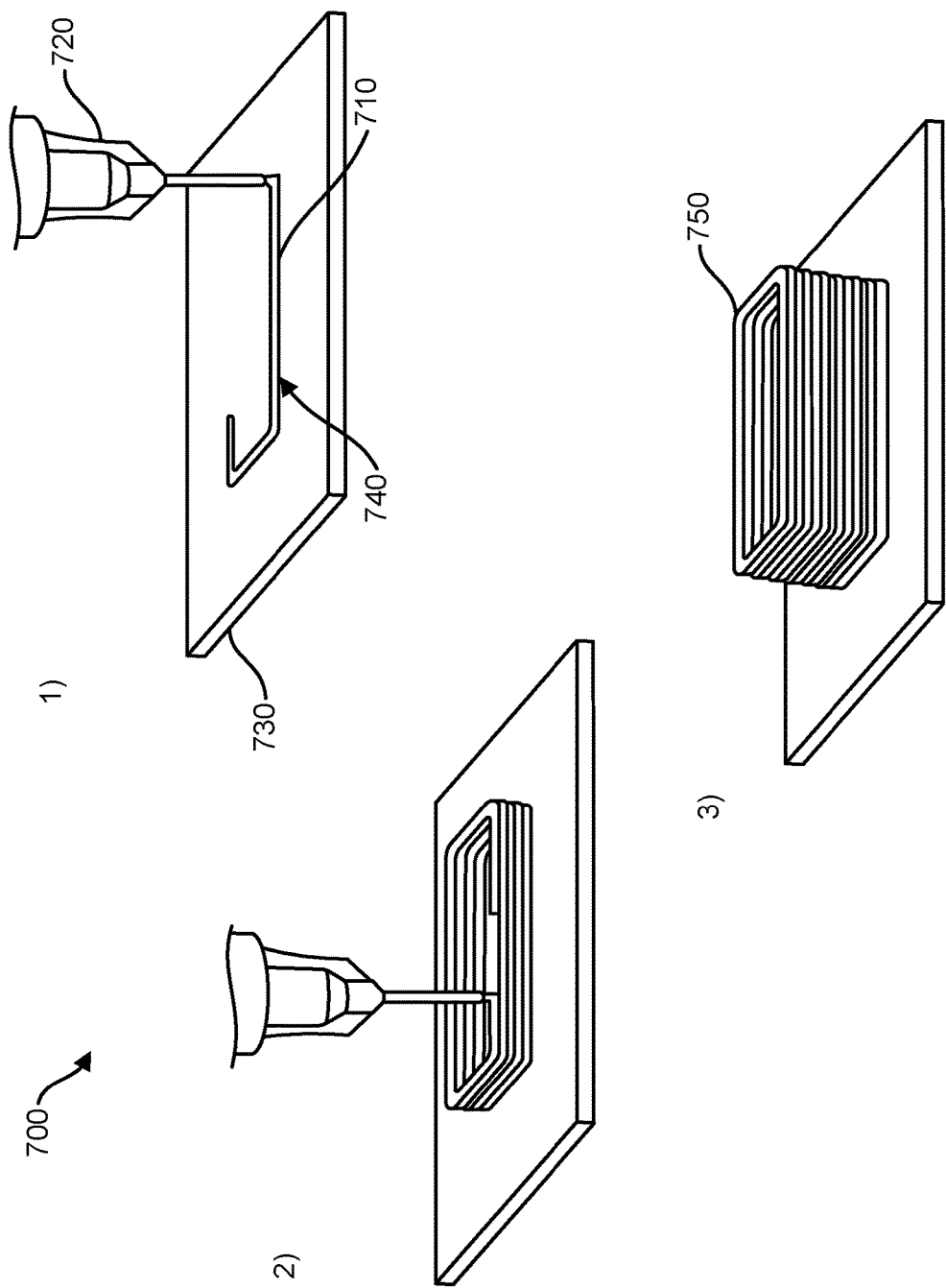
FIG. 7 illustrates a fused deposition modeling manufacturing process for producing a bioscaffold structure, in accordance with various embodiments.
Figure 10:
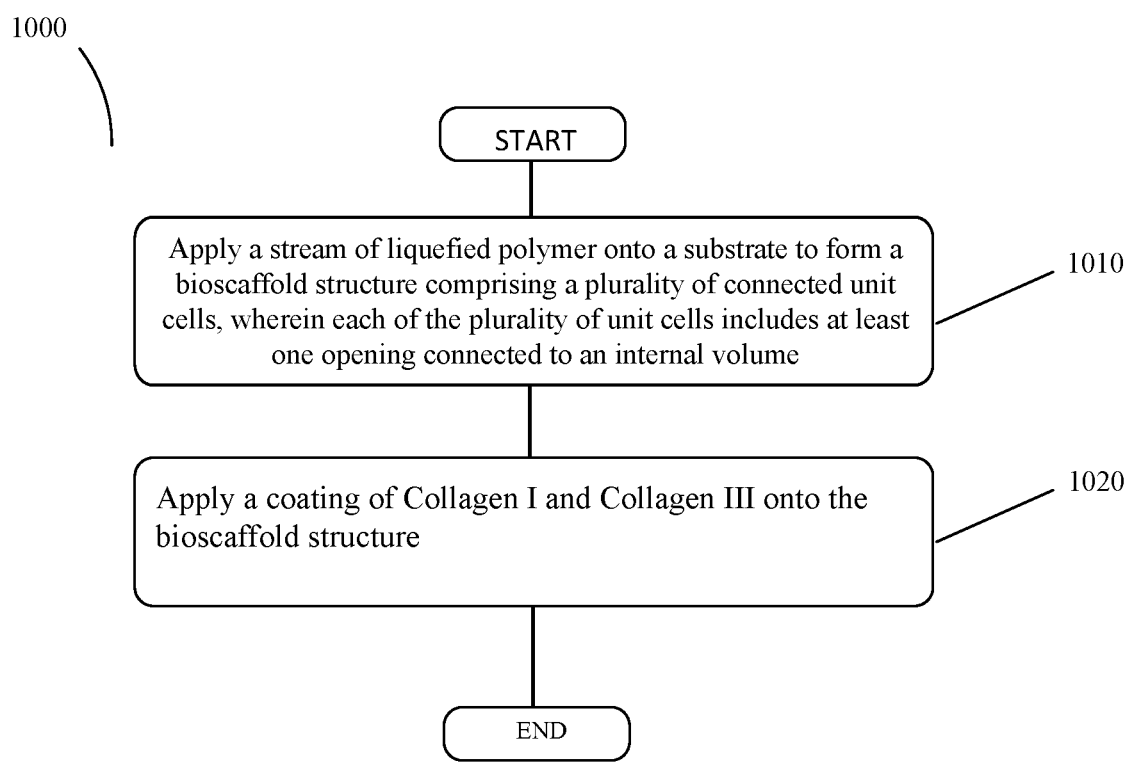
FIG. 10 is a flowchart illustrating a process for producing a bioscaffold structure, in accordance with various embodiments.

In accordance with various embodiments, a method for producing a bioscaffold structure is provided as illustrated in FIG. 7 and provided for by method 1000 of FIG. 10. As provided in FIG. 10, method 1000 can comprise, at step 1010, applying a stream of liquefied polymer onto a substrate form a bioscaffold structure comprising a plurality of connected unit cells, wherein each of the plurality of unit cells includes at least one opening connected to an internal volume. In various embodiments, the liquefied polymer is comprised of a solution or mixture containing one or more polymer components. In various embodiments, the liquefied polymer is comprised of a polymer material that has been heated beyond its melting point to a fluid state.

In various embodiments, step 1010 can be repeated such that the streams of liquefied polymer are successively deposited on top of each other to form the bioscaffold structure.

Method 1000 further comprises, at step 1020, applying a collagen (e.g., Collagen I, Collagen II, Collagen III, Collagen IV, Collagen V, etc.) coating onto the bioscaffold structure. In various embodiments, the applied collagen coating is deposited on the external surfaces (i.e., outside surfaces) and internal surfaces (e.g., pores, pore volume surfaces, etc.) of the bioscaffold structure.

In various embodiments, the collagen coating includes Collagen I and Collagen III. In various embodiments, the collagen coating can contain a Collagen I to Collagen III ratio similar to those contained within fetal and adolescent dermis. Conventional tissue offerings, which are predominantly taken from adult and elderly donors, contain a higher ratio (i.e., greater than about 2.4) of Collagen I to Collagen III, thereby providing decreased support, cushioning, protection, reinforcement and covering than do tissues containing lower ratios.

In various embodiments, the collagen coating can have a Collagen I to Collagen III ratio in the range of between about 0.5 to about 3.5, or in the range of between about 0.75 to about 3.0, or in the preferred range of between about 0.9 to about 2.5. The preferred Collagen I to Collagen III ratio range of between about 0.9 to about 2.5 may offer advantages against conventional tissue offerings, which are predominantly taken from adult and elderly donors, contain much higher ratios of Collagen I to Collagen III, thereby providing decreased support, cushioning, protection, reinforcement and covering than do tissues containing lower ratios.

More specific ratios of Collagen I to Collagen III can include about 0.5, about 0.55, about 0.6, about 0.65, about 0.7, about 0.75, about 0.8, about 0.85, about 0.9, about 0.95, about 1.0, about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 1.95, about 2.0, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3.0, about 3.05, about 3.1, about 3.15, about 3.2, about 3.25, about 3.3, about 2.35, about 3.4, about 3.45, about 3.5 and ranges between any two of these values.

In various embodiments, the collagen (e.g., Collagen I, Collagen II, Collagen III, Collagen IV, Collagen V, etc.) and/or other ECM materials can be combined with the liquefied polymer to form a bioink that can be deposited to form the bioscaffold structure in a single process step instead of successive process steps.

In various embodiments, the collagen and/or ECM material coating can be lypholized to sublime the solvent used to create the suspension thus allowing the collagen and/or ECM material coating to adhere to the bioscaffold structure.

In various embodiments, the bioscaffold structure can be scanned with an electron beam, UV light or chemical agent such as EDAC, carbodiimide (or other physical or chemical crosslinker prior to the application of the collagen and/or ECM material coating in order to crosslink the polymers and increase the structural strength and integrity of the bioscaffold structure.

In various embodiments, the at least one opening of each of the plurality of unit cells can have a diameter of between about 100 microns to about 500 microns. Moreover, each of the plurality of unit cells can comprise filaments that have a diameter of less than or equal to about 100 microns. The plurality of connected unit cells can also form a substantially planar sheet. Further, the plurality of connected unit cells can form a 3D macrostructure. The 3D macrostructure can include, for example, a "hand in glove" fit configuration and a "ready-to-use" solid implant configuration discussed in more detail above.

As illustrated in FIG. 7, step (1), a stream of liquefied polymer 710 can be deposited, via syringe or nozzle (or any other stream deposition device) 720, onto a substrate 730. The liquid polymer stream 710 can form a single layer 740. As shown in step (2), the depositing process can be repeated to add additional liquefied polymer layers to increase the thickness of the liquefied polymer deposition until a desired thickness is achieved for a finished product 750, as provided in step (3). The liquefied polymer streams can form a single or multiple layer(s) comprised of a plurality of unit cell structures. The finished product can be, as discussed above, a substantially planar sheet or a 3D macrostructure.

Each unit cell of the bioscaffold structure can comprise a polymer with a collagen coating. The polymer can be polycaprolactone. The composition that is deposited can be in the form of a slurry of polymer with the Collagen I/Collagen III embedded, mixed, or encapsulated with the polymer. Alternatively, a coating of Collagen I/Collagen III and streams of liquefied polymer can be deposited separately and then interlaced to form the structure. The deposition can be performed, for example, by a bioprinter using components such as, for example, a nozzle or syringe. These components can be, for example, pneumatically, piston, or screw driven. Pneumatic driven syringes, for example, can deposit liquefied polymer in sequential layers to create the construct, which will ultimately be crosslinked. Bioactive molecules (e.g., Collagen I/Collagen III based bioinks with any other additional bioactive components as discussed above) can either be co-printed along with the base polymer or layered upon the base polymer layer sequentially.

As compared to traditional polymer-based compositions, which can be deposited via additive manufacturing techniques under heated conditions and relatively higher pressures to promote scaffold formation while still maintaining structural stability of the polymer-based composition, certain bioinks containing bioactive molecules in addition to polymers may have to be deposited under milder conditions relative to polymer-based compositions. This can be due to the relatively more delicate nature of bioink structures (e.g., higher water content, non-crystalline structure, etc.). As such, bioprinting process parameters such as printing pressure or nozzle/syringe diameter can be considered in reducing the shear stress on some bioinks to prevent damaged or lysed cells, which can affect cell viability in the bioinks. Other parameters that may be considered, and correspondingly controlled include, for example, printing temperature (e.g., lower temperature than polymer-based compositions), uniformity in diameter of the filaments that make up the unit cell, angles at the interaction of filaments, bleeding of filaments together at intersects, and maintenance of shape fidelity after printing but before cross-linking with polymer-based compositions. Therefore, and in accordance with various embodiments, the polymer and bioactive molecules (e.g., Collagen I/Collagen III and any other additional bioactive components as discussed above) can be deposited as, for example, droplets or streams (see below for more detail) separately utilizing separately defined process parameters to ensure scaffold manufacturing while maintaining structural integrity of each respective deposited compositions. The deposition of the polymers and bioactive molecules (e.g., Collagen I/Collagen III and any other additional bioactive components as discussed above) can occur, as stated above, separately and then interlaced or crosslinked to form the scaffold. To accomplish this, the bioactive molecules can either be co-printed along with the base polymer or layered upon the base polymer layer sequentially.

In accordance with various embodiments, bioscaffold structures can be manufactured by deposition process using a bioprinter such as a CELLINK™ (Palo Alto, CA) or REGENHU™ Bioprinter (REGENHU™, Switzerland). The bioprinter can be set up to allow for the printing of polymer via pneumatic driven syringes (or nozzle) via a fused deposition modeler, which will allow for the deposition (or extrusion) of molten polymer. Polymer strands will be pressure deposited using a needle to create the individual layer and complete the bioscaffold structure to pre-determined specifications as to properties such as, for example, pore size, angular filament deposition range, density, height, polymer type and filament size (e.g., diameter). For example, polymer strands can be deposited in a raster pattern with raster angles between about 10 and about 90 degree orientations relative to each other (also referred to as angular range) to create a bioscaffold structure having a pore size of between about 100 to about 500 micron pores Moreover, in accordance with various embodiments, Collagen I/Collagen III (SIGMA ALDRICH™, MO or R&D SYSTEMS™, MN) containing coating can be deposited within the construct either in tandem (co-printed) in a similar fashion to the polymer, or as a sequential layer (such as a coating or surface modification following polymer deposition). Following printing, the polymer construct and Collagen I/Collagen III coating (and any other further added bioactive materials such as those discussed above) can be crosslinked using, for example, calcium chloride ($CaCl_2$), ultraviolet (UV) or other methods.

The deposited strands (fibers or fibrils) can be substantially parallel. Adjacent strands can be deposited substantially perpendicular to each other (i.e., in a raster pattern). Each strand can be deposited at an angular range of between about 10 to about 90 degrees relative to the adjacent strand. The deposited strands can have a random orientation across the layer.

In accordance with various embodiments, the step of depositing a plurality of strands to form a layer can further comprise repeating the depositing step to form a plurality of layers of polymer material. Adjacent strands of at least one layer can be deposited substantially perpendicular to each other. Each strand of at least one layer can be deposited at an angular range of between about 10 to about 90 degrees relative to the adjacent strand. The strands of at least one layer can have a random orientation across the layer. The deposited strands, of the plurality of layers, can be substantially parallel.

In accordance with various embodiments, the strands of each layer are substantially parallel. For example, for a three-layer bioscaffold structure, the strands of the first layer are parallel to each other, the strands of the second layer are parallel to each other, and the strands of the third layer are parallel to each other. The strands on at least one layer can be deposited substantially perpendicular to strands of another layer. The strands on at least one layer can be deposited substantially perpendicular to strands of an adjacent layer. The strands on at least one layer can be deposited at an angular range of between about 10 to about 90 degrees relative to strands of another layer. The strands on at least one layer can be deposited at an angular range of between about 10 to about 90 degrees relative to strands of an adjacent layer. The strands of each layer can have a random deposition angle. The random deposition angle can have an angular range between about 10 to about 90 degrees.

It has been found that by controlling variation of particular properties of the bioscaffold structure, discussed above, and testing the cellular response to those bioscaffold microgeometries, one can allow for determination of an ideal geometry for optimizing parameters such as, for example, cellular infiltration, cellular attachment, cellular survival, cellular fate and cellular regeneration/remodeling (discussed in detail above). These properties include pore size (e.g., by varying distance between printed filaments), pore shapes (e.g., by varying the degree of orientation in which filaments are perpendicularly printed to each other, or varying the base unit cell geometry used), filament size (e.g., by varying the gauge of needle/syringe/nozzle with which filaments are printed), elastic modulus of the filaments (e.g., by printing with various polymers, polymer combinations, polymer types such as synthetic and natural), thickness of the bioscaffold structure (e.g., by printing varying sequential layers of the construct or number of layers), and arrangement of fibers (e.g., by printing a random arrangement of fibers vs. organized and repeating structures).

Tests to determine effectiveness of the constructs (appropriateness of the optimal microenvironment provided by the micro-geometric structures) include, for example, in vitro cellular migration assays, in vitro cellular attachment (staining and Western Blotting), in vitro cellular survival and proliferation assays (proliferating cell nuclear antigen, propidium iodide), in vitro cell fate analysis (vimentin, alpha smooth muscle actin), and in vitro collagen synthesis in response to culture on the construct (hydroxyproline assay, Sirius red/FCF green).

Although specific embodiments have been described in this specification, these embodiments and applications are exemplary only, and many variations are possible. It will be understood that, while specific combinations of elements, components and orders of process operations (i.e., method steps) are described in detail, these examples are not intended to be limiting, and all such variations and modifications as would be apparent to one of ordinary skill in the art are intended to fall within the scope of this disclosure. For example, although the manufacturing processes disclosed above are described as a sequential order of process operations, each process operation can occur in any order depending on the specific requirements of the manufacturing process.

What is claimed:

1. A bioscaffold structure, comprising:
a plurality 3D printed polymers;
a plurality of connected unit cells formed from the plurality of 3D printed polymers, wherein each of the plurality of unit cells includes at least one opening connected to an internal volume; and
wherein the plurality of connected unit cells is at least partially coated with a collagen coating comprising a Collagen I to Collagen III ratio of between about 0.75:1 to about 3.5:1.

2. The bioscaffold structure of claim 1, wherein the at least one opening has a diameter of between about 100 microns to about 500 microns.

3. The bioscaffold structure of claim 1, wherein the plurality of unit cells have a plurality, wherein each filament of the plurality of filaments of the unit cells has a diameter of less than about 100 microns.

4. The bioscaffold structure of claim 3, wherein each filament comprises an extracellular material containing a polymer.

5. The bioscaffold structure of claim 4, wherein the polymer is polycaprolactone.

6. The bioscaffold structure of claim 1, wherein the plurality of connected unit cells form a substantially planar sheet.

7. The bioscaffold structure of claim 1, wherein the plurality of connected unit cells form a 3D macrostructure.

8. The bioscaffold structure of claim 1, wherein the bioscaffold structure has a tensile strength of between about 10 N/cm to about 200 N/cm.

9. The bioscaffold structure of claim 1, wherein the bioscaffold structure has a stiffness of less than about 80 N/mm.

10. The bioscaffold structure of claim 1, wherein the bioscaffold structure has a maximum load of greater than about 50N.

11. The bioscaffold structure of claim 1, wherein the bioscaffold structure has a tensile stress limit of about 3 MPa to about 100 MPa.

12. The bioscaffold structure of claim 1, wherein the bioscaffold structure has a tensile strain limit of greater than about 10%.

13. The bioscaffold structure of claim 1, wherein the bioscaffold structure has a modulus of elasticity of about 10 MPa to about 450 MPa.

14. The bioscaffold structure of claim 1, wherein the bioscaffold structure has a thickness of between about 0.6 mm to about 2.5 mm.

15. A bioscaffold structure, comprising:
a plurality of 3D printed polymers;
a plurality of connected unit cells formed from the plurality of 3D printed polymers, wherein each of the plurality of unit cells includes at least one opening connected to an internal volume and wherein the plurality of connected unit cells makes up a layer of fibers composed of an extracellular material containing a Collagen I to Collagen III ratio of between about 0.75:1 to about 3.5:1; and
wherein the layer includes a plurality of pores.

16. The bioscaffold structure of claim 15, wherein the plurality of pores have diameters that are substantially equal.

17. The bioscaffold structure of claim 15, wherein each fiber has a diameter of less than about 100 microns.

18. The bioscaffold structure of claim 15, wherein the layer has a thickness of between about 0.6 mm to about 2.5 mm.

19. The bioscaffold structure of claim 15, wherein each of the plurality of pores has a diameter that is between about 100 microns to about 500 microns.

20. The bioscaffold structure of claim 15, wherein the extracellular material further contains a polymer.

21. The bioscaffold structure of claim 20, wherein the polymer is polycaprolactone.

22. The bioscaffold structure of claim 15, wherein the layer forms part of a substantially planar sheet.

23. The bioscaffold structure of claim 15, wherein the layer forms part of a 3D macrostructure.

24. The bioscaffold structure of claim 15, wherein the layer has a tensile strength of between about 10 N/cm to about 200 N/cm.

25. The bioscaffold structure of claim 15, wherein the layer has a stiffness of less than about 80 N/mm.

26. The bioscaffold structure of claim 15, wherein the layer has a maximum load of greater than about 50N.

27. The bioscaffold structure of claim 15, wherein the layer has a tensile stress limit of about 3 MPa to about 100 MPa.

28. The bioscaffold structure of claim 15, wherein the layer has a tensile strain limit of greater than about 10%.

29. The bioscaffold structure of claim 15, wherein the layer has a modulus of elasticity of about 10 MPa to about 450 MPa.

30. The bioscaffold structure of claim 15, wherein the layer has a thickness of about 0.6 mm to about 2.5 mm.

* * * * *